US009080180B2

(12) United States Patent
Sawada et al.

(10) Patent No.: US 9,080,180 B2
(45) Date of Patent: Jul. 14, 2015

(54) TRANSGENIC PLANTS EXPRESSING STX2EB PROTEIN FOR USE AS A PIG EDEMA DISEASE VACCINE

(75) Inventors: Kazutoshi Sawada, Sodegaura (JP); Kazuya Yoshida, Nara (JP); Mayumi Yoshida, legal representative, Nara (JP); Nobuo Yoshida, legal representative, Nishinomiya (JP); Kyoko Yoshida, legal representative, Nishinomiya (JP); Takeshi Matsui, Ikoma (JP); Sou-ichi Makino, Obihiro (JP); Keiko Kawamoto, Obihiro (JP)

(73) Assignees: IDEMITSU KOSAN CO., LTD., Tokyo (JP); NATIONAL UNIVERSITY CORPORATION NARA INSTITUTE OF SCIENCE AND TECHNOLOGY, Ikoma-shi (JP); NATIONAL UNIVERSITY CORPORATION OBIHIRO UNIVERSITY OF AGRICULTURE AND VETERINARY MEDICINE, Obihiro-shi (JP)

( * ) Notice: Subject to any disclaimer, the term of this patent is extended or adjusted under 35 U.S.C. 154(b) by 882 days.

(21) Appl. No.: 12/667,393

(22) PCT Filed: Mar. 25, 2008

(86) PCT No.: PCT/JP2008/055550
§ 371 (c)(1),
(2), (4) Date: Sep. 20, 2010

(87) PCT Pub. No.: WO2009/004842
PCT Pub. Date: Jan. 8, 2009

(65) Prior Publication Data
US 2011/0002950 A1    Jan. 6, 2011

(30) Foreign Application Priority Data
Jul. 3, 2007    (JP) ................................. 2007-174919

(51) Int. Cl.
*C12N 15/82*    (2006.01)
*C12N 15/30*    (2006.01)
*A61K 39/112*    (2006.01)
*A61K 39/108*    (2006.01)
*A61K 39/00*    (2006.01)

(52) U.S. Cl.
CPC ........ *C12N 15/8258* (2013.01); *A61K 39/0258* (2013.01); *C12N 15/8257* (2013.01); *A61K 2039/517* (2013.01); *A61K 2039/552* (2013.01)

(58) Field of Classification Search
None
See application file for complete search history.

(56) References Cited

U.S. PATENT DOCUMENTS

| 5,294,593 | A | * | 3/1994 | Khan ............................. 504/100 |
| 5,436,394 | A | | 7/1995 | Willmitzer et al. |
| 5,908,975 | A | | 6/1999 | Caimi et al. |
| 5,917,127 | A | | 6/1999 | Willmitzer et al. |
| 6,054,637 | A | | 4/2000 | Boller et al. |
| 6,391,638 | B1 | | 5/2002 | Shaaltiel |
| 7,268,275 | B2 | | 9/2007 | Ffrench-Constant et al. |
| 2002/0110915 | A1 | | 8/2002 | Shaaltiel |
| 2003/0191076 | A1 | | 10/2003 | Wesselingh et al. |
| 2004/0103455 | A1 | | 5/2004 | Ffrench-Constant et al. |
| 2005/0032211 | A1 | | 2/2005 | Shaaltiel |
| 2006/0204487 | A1 | | 9/2006 | Shaaltiel et al. |
| 2008/0038232 | A1 | | 2/2008 | Shaaltiel et al. |
| 2008/0168588 | A1 | | 7/2008 | Ffrench-Constant et al. |
| 2009/0053762 | A1 | | 2/2009 | Shaaltiel |
| 2009/0208477 | A1 | | 8/2009 | Shaaltiel |

FOREIGN PATENT DOCUMENTS

| EP | 1 057 895 A1 | | 12/2000 | |
| JP | 5 49482 | | 3/1993 | |
| JP | 9 505467 | | 6/1997 | |
| JP | 2003 79372 | | 3/2003 | |
| JP | 2003 116385 | | 4/2003 | |
| JP | 2003 180354 | | 7/2003 | |
| JP | 2004 506432 | | 3/2004 | |
| JP | 2003079372 A1 | * | 11/2005 | |
| JP | 2006 515169 | | 5/2006 | |
| JP | 2006 524506 | | 11/2006 | |
| WO | WO 99/18225 | | 4/1999 | |
| WO | WO 0075345 | * | 6/2000 | ........... C07K 14/245 |
| WO | 00 75345 | | 12/2000 | |
| WO | 01 52886 | | 7/2001 | |

OTHER PUBLICATIONS

Matsui et al. High-efficiency secretory production of peroxidase C1a using vesicular transport engineering in transgenic tobacco. (2006) J. of Bioscience and Bioengineering; vol. 102; pp. 102-109.*
Makino et al. Genetically modified Shiga toxin 2e (Stx2e) producing *Escherichia coli* is a vaccine candidate for porcine edema disease. (2001) Micoriol Pathogenesis; vol. 31; pp. 1-8.*
O'Dowd et al, Vaccine 17:1442-1453, 1999.*
Kim et al, Microbiol. Immunol. 41(10), p. 805-808, 1997.*
Twyman et al, TRENDS in Biotech, 21(12), p. 570-578, 2003.*
Okushima et al, Plant Mol. Biol 42(3), p. 479-488, 2000.*
Genbank Accession, Okushima et al 2000.*

(Continued)

*Primary Examiner* — Cathy Kingdon Worley
*Assistant Examiner* — Stephen Uyeno
(74) *Attorney, Agent, or Firm* — Oblon, McClelland, Maier & Neustadt, L.L.P.

(57) ABSTRACT

A technology for producing a pig edema disease vaccine at low cost and at high efficiency is developed. Specifically, a gene of a pig edema disease toxin protein (Stx2e protein) is efficiently expressed in plant cells to produce a plant vaccine for pig edema disease at low cost. An Stx2e protein including a secretory signal peptide derived from a plant added at an amino terminus is expressed in cells of a plant such as *Lactuca sativa* using the 5'-untranslated region of an alcohol dehydrogenase gene (ADH5'UTR) derived from a plant.

14 Claims, 27 Drawing Sheets

(56) References Cited

OTHER PUBLICATIONS

Genbank Accession, Kato et al, 2003.*
Ong et al, Molecular Microbiology, 43(3), p. 665-676, 2003.*
Genbank Accession, Kim et al 1997.*
Johannes et al (JBC, 272(21), pp. 19554-19561, 1997).*
U.S. Appl. No. 12/990,597, filed Nov. 1, 2010, Sawada, et al.
Xue Qin Ran, et al., "The immunogenicity of fusion protein linking the carboxyl terminus of the B subunit of Shiga toxin 2 to the B subunit of *E. coli* heat-labile enterotoxin", Veterinary Microbiology, vol. 127, No. 1-2, XP022393837, 2008, pp. 209-215.
Federica Brandizzi, et al., "ER quality control can lead to retrograde transport from the ER lumen to the cytosol and the nucleoplasm in plants", The Plant Journal, vol. 34, No. 3, XP9131982, May 2003, pp. 269-281.
Hongli Liu, et al., "The Strategies of Transgenic Plant Vaccine", China Biotechnology, vol. 24, 2004, pp. 30-33 (With English Translation).
Matsui, Takeshi et al., "High-Efficiency Secretory Production of Peroxidase Cla Using Vesicular Transport Engineering in Transgenic Tobacco", Journal of Bioscience and Bioengineering, vol. 102, No. 2, pp. 102-109, Aug. 2006.
Makino, Sou-Ichi et al., "Genetically modified Shiga toxin 2e (Stx2e) producing *Escherichia coli* is a vaccine candidate for porcine edema disease", Microbial Pathogenesis, vol. 31, No. 1, pp. 1-8, (2001).
Kim, Tae-Geum et al., "Synthesis and assembly of *Escherichia coli* heat-labile enterotoxin B subunit in transgenic lettuce (*Lactuca sativa* )", Protein Expression and Purification, vol. 51, No. 1, pp. 22-27, Jan. 2007.
Sawada, Kazutoshi et al., "3-7 Development of Vaccine Component Production Technology by Lettuce", Preprints of Biotechnology Symposium, vol. 23, pp. 107 to 108, Nov. 6, 2007.
Sawada, Kazutoshi et al., "Research and Development of Producing Vaccine Protein for Domestic Animals by Recombinant Lettuce", Preprints of Biotechnology Symposium, vol. 23, pp. 28 to 31 , Nov. 6, 2007.
Matsui, Takeshi et al., "Production of Pig Edema Disease Vaccine Producing Lettuce for the Plant Factory", Abstracts of the Annual Meeting of the Society for Biotechnology, vol. 59, p. 146, Aug. 2, 2007.
Kang, Tae-Jin et al., "Enhanced Expression of B-Subunit of *Escherichia coli* Heat-Labile Enterotoxin in Tobacco by Optimization of Coding Sequence", Applied Biochemistry and Biotechnology, vol. 117, No. 3, pp. 175-187, (2004).
Satoh, Junko et al., "The 5'-Untranslated Region of the Tobacco Alcohol Dehydrogenase Gene Functions as an Effective Translational Enhancer in Plant", Journal of Bioscience and Bioengineering, vol. 98, No. 1, pp. 1-8, (2004).

* cited by examiner

Fig. 3

```
stx2eB    ATGGCGGGCGGATTGTGCTAAAGGTAAAATTGAGTTTTCCAAGTATAATGAGGATAATACC
mstx2eB1  ATGGCAGCAGATTGCGCTAAGGGTAAGATTGAGTTCTCCAAGTACAACGAGGATAACACC
mstx2eB2  ATGGCAGCAGATTGTGCAAAAGGTAAAATTGAATTTTCTAAATATAATGAAGATAATACA
mstx2eB3  ATGGCCCCGACTGCGCCAAGGGGAAGATCGAGTTCTCCAAGTACAACGAGGACAACACC
mstx2eB4  ATGGCCGCCGATTGCGCCAAGGGCCAAGGGTAAGATCGAATTCTCCAAGTACAACGAAGATAACACT
          **      * stx2eB    TTTACTGTGAAGGTGTCAGGAAGAGAATACTGGACCAACAGATGGAATTTGCAGCCATTG
mstx2eB1  TTCACAGTGAAGGTGTCAGGAAGGTACTGGACAACAGGTGGAACTTGCAACCATTG
mstx2eB2  TTTACAGTTAAAGTTTCTGGTAGAGAATATTGGACAAATAGATCTTCAACCACTT
mstx2eB3  TTCACCCGTGAAGGTGTCCGGGAGGGAGTACTGGACGGAACAACAGGTGGAACCTCCAGCCCTC
mstx2eB4  TTCACTGTTAAGGTTTCCGGTCGTGAATACTGGACTGTCCAACCGTTGGAACCTTCCAACCACTC
          *      **     *    **        *** * stx2eB    TTACAAAGTGCTCAGCTGACAGGGATGACTGTAACAATCATATCTAATACCTGCAGTTCA
mstx2eB1  TTGCAAAGCGCTCAACTCACACACTTACAGTGACAGGAGTATGACAGTTACCTGCAGTCA
mstx2eB2  CTTCAATCTGCACACTTCGCCCAGCTGACCTATGACTGACAGGTACAATTATTTCTAATACATGTCTTCT
mstx2eB3  CTCCAGTCCGCGCCCAGCTCCCAGCTGACCTGACCGTGACCATCATCTCCAACACCTGCTCCTCC
mstx2eB4  CTCCAATCCGCCCAACTCCACTGGTATGACTGTTACTACTGTTACTACATCTCCAACACTTGCTCCTCC
          *          *     * stx2eB    GGCTCAGGCTTTGCCCAGGTGAAGTTTAAC
mstx2eB1  GGGTCAGGGTTCGCCCAAGTGAAGTTCAAC
mstx2eB2  GGTTCTGGTTTTGCACAAGTTAAATTTAAT
mstx2eB3  GGGTCCGGGTTCGCCCAGGTGAAGTTCAAC
mstx2eB4  GGTTCCGGTTTCGCCCAAGTTAAGTTCAAC
          *  ** ** ** ** ** ** ** ** **
```

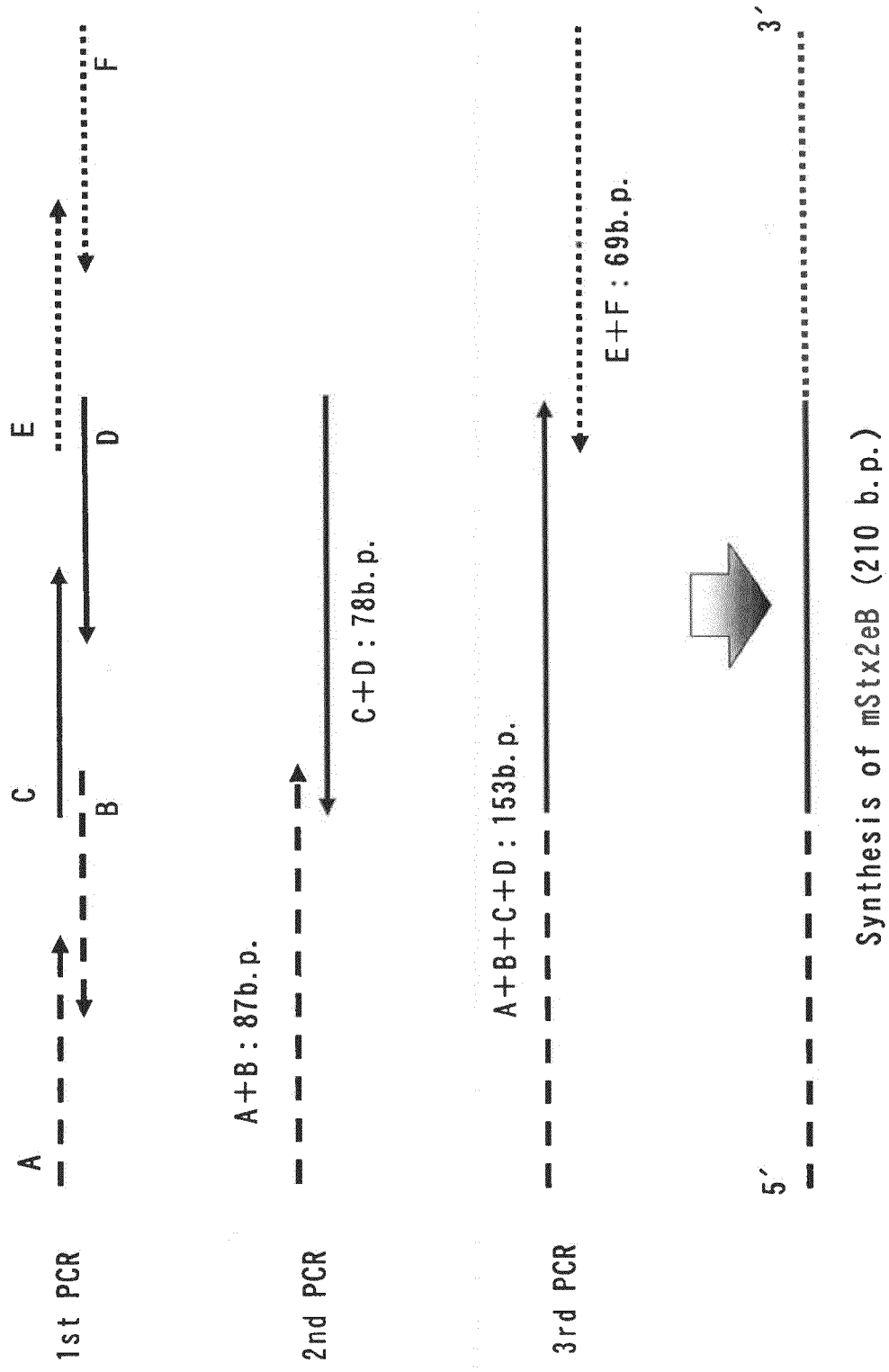

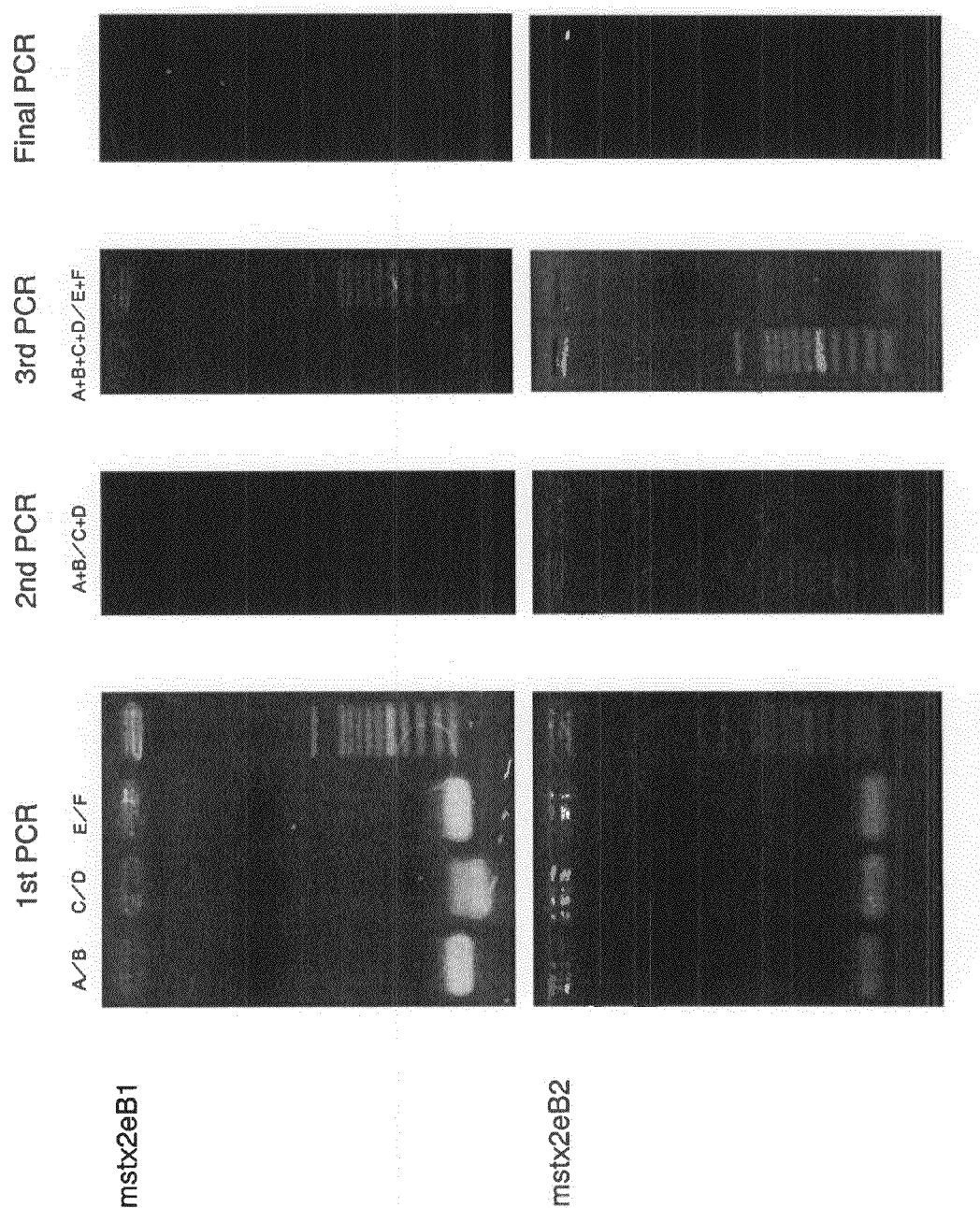

Fig. 7

Kozak-ER-stx2eA

ADH-ER-stx2eA

```
Stx2eB    ATG GCG GCG GAT TGT GCT AAA GGT AAA ATT GAG TTT TCC AAG TAT AAT GAG GAT AAT ACC
mStx2eB5  ATG GCG GCG GAC TGC GCG AAG GGC AAG ATC GAG TTC TCG AAG TAC AAC GAG GAC AAC ACG
          *** ** ** **  **  **  **  **  **  **  **  **  **  **  **  **  **  **  **  **

Stx2eB    TTT ACT GTG AAG GTG TCA GGA AGA GAA TAC TGG ACG AAC AGA TGG AAT TTG CAG CCA TTG
mStx2eB5  TTC ACG GTC AAG GTC TCG CGC CGC GAG TAC TGG ACG AAC CGC TGG AAC CTG CAG CCG CTG
          **  **  **  **  **  **   *   *  **  **  *** **  **   *  **   *  **  **   *

Stx2eB    TTA CAA AGT GCT CAG CTG ACA GGG ATG ACT GTA ACA ATC ATA TCT AAT ACC TGC AGT TCA
mStx2eB5  CTG CAG CAG GCG CAG CTG ACG ACG ATG ACG GTC ACG ATC ATC TCG AAC ACG TGC TCG TCG
           *  **  **  **  **  **  **  **  *** **  **  **  **  **  **  **  **  **  **  **

Stx2eB    GGC TCA GGC TTT GCC CAG GTG AAG TTT AAC
mStx2eB5  GGC TCG GGC TTC GCG CAG GTC AAG TTC AAC
                            
```

TRANSGENIC PLANTS EXPRESSING STX2EB PROTEIN FOR USE AS A PIG EDEMA DISEASE VACCINE

CROSS-REFERENCE TO RELATED APPLICATIONS

The present application is a 35 U.S.C. §371 National Stage patent application of International patent application PCT/JP2008/055550, filed on Mar. 25, 2008, which claims priority to Japanese patent application JP 2007-174919, filed on Jul. 3, 2007.

TECHNICAL FIELD

The present invention relates to a DNA construct for producing a pig edema disease vaccine, a pig edema disease vaccine containing a transformant transformed with the DNA construct, and a method of controlling pig edema disease using the pig edema disease vaccine.

BACKGROUND ART

Pig edema disease is a bacterial disease caused by rapid proliferation of *Escherichia coli* having an Stx2e (edema disease bacterium) in the upper intestinal tract, resulting in absorption of the toxin into blood and is known to occur at a high incidence in baby pigs one or two weeks later of weaning. The fatality of the infection with an edema disease bacterium is very high (50 to 90%). Currently, various antibiotics are used for controlling edema disease, but use of the antibiotics is limited because of problems such as emergence of drug-resistant bacteria.

Because of this situation, studies on pig edema disease vaccines have been made to provide a method of efficiently preventing pig edema disease. For example, a case where pigs are immunized with a detoxified edema disease bacterium-toxin protein to prevent death caused by infection of the edema disease bacterium has been reported (Non-patent Document 1). In this case, a detoxified edema disease bacterium-toxin protein is produced by a recombinant *Escherichia coli* and inoculated into the pigs. However, this method has a problem of not achieving a low cost from the viewpoint of practical application of a pig edema disease vaccine because an insufficient amount of the detoxified edema disease bacterium-toxin protein produced by the recombinant *Escherichia coli* and the need of inoculation of the vaccine by direct injection or nasal spray of the protein requires labor of the human.

Meanwhile, studies have been made on production of a useful substance by a plant using a transgenic technology. For example, production of B-subunit of *Escherichia coli* heat-labile toxin (LT) protein by *Lactuca sativa* has been reported (Non-patent Document 2). In this study, a B-subunit gene of a codon-modified LT protein is expressed in *Lactuca sativa* using a cauliflower mosaic virus 35S RNA promoter (CaMV35S) serving as a promoter, which is expressed in a plant at a high level, and Kozak sequence serving as an enhancer. As a result, it has been reported that B-subunit of the LT protein is accumulated in an amount of about 2.0% by mass based on the total soluble proteins of *Lactuca sativa*. However, the amount of the protein accumulated is considered to be insufficient to efficiently control a bacterial disease using a transgenic plant. That is, it is necessary to efficiently produce and accumulate a target protein in plant cells by expressing the gene of the target protein at a high level.

On the other hand, the base sequence of the 5'-untranslated region (NtADH5'UTR) of an alcohol dehydrogenase gene derived from *Nicotiana tabacum* is known to be an enhancer capable of acting in *Arabidopsis thaliana* or *Oriza sativa* (Patent Documents 1 and 3). However, a case where a gene encoding a bacterial toxin protein is expressed using the base sequence of NtADH5'UTR has not been reported.

[Non-patent Document 1] Makino et al., Microbial Pathogenesis, Volume 31, Number 1, July 2001, pp. 1-8(08)

[Non-patent Document 2] Kim et al., Protein Expression and Purification, Volume 51, Number 1, January 2006, pp. 22-27(06)

[Patent Document 1] JP 2003-79372 A

[Non-patent Document 3] Satoh et al., The 5'-untranslated region of the tobacco alcohol dehydrogenase gene functions as an effective translational enhancer in plant. J. Biosci. Bioeng. (2004)98, 1-8

DISCLOSURE OF THE INVENTION

It is an object of the present invention to provide a technology for producing a pig edema disease vaccine at low cost and at high efficiency. Specifically, an object of the present invention is to produce a plant vaccine for pig edema disease at low cost by efficiently expressing in plant cells a gene of a toxin protein of pig edema disease (Stx2e protein).

The inventors of the present invention have found out that an Stx2e protein including a secretory signal peptide derived from a plant added at the amino terminus is expressed by using the 5'-untranslated region of an alcohol dehydrogenase gene derived from a plant (ADH5'UTR), with a result that the Stx2e protein can be efficiently expressed in a plant such as *Lactuca sativa* and the protein can be accumulated in a plant at a high level, thus completing the present invention. That is, the present invention is as follows.

A first invention relates to a DNA construct including a 5'-untranslated region of an alcohol dehydrogenase gene derived from a plant and a DNA encoding an Stx2e protein added with a secretory signal peptide derived from a plant at an amino terminus and operably-linked to the region (hereinafter, referred to as "DNA construct of the present invention" in some cases).

The 5'-untranslated region of the alcohol dehydrogenase gene is preferably derived from *Nicotiana tabacum*. In addition, the secretory signal peptide is preferably derived from *Nicotiana tabacum*. The Stx2e protein is preferably a B-subunit of the Stx2e protein.

In addition, the Stx2e protein preferably includes an endoplasmic reticulum retention signal peptide or a vacuolar transport signal peptide added at a carboxyl terminus. The endoplasmic reticulum retention signal peptide preferably includes a KDEL sequence (SEQ ID NO: 13) or an HDEL sequence (SEQ ID NO: 14) at the carboxyl terminus. The vacuolar transport signal peptide is preferably derived from *Nicotiana tabacum*.

In addition, the DNA construct of the present invention preferably includes a base sequence represented by any of SEQ ID NOS: 12, 23, 24, 75, 77, 78, and 86.

A second invention relates to a recombinant vector including the DNA construct of the present invention (hereinafter, referred to as "vector of the present invention" in some cases).

A third invention relates to a transformant transformed with the recombinant vector of the present invention (hereinafter, referred to as "transformant of the present invention" in some cases).

The transformant of the present invention is preferably a transformed plant cell or a transformed plant. In addition, the plant is preferably *Lactuca sativa*.

A fourth invention relates to a seed obtained from the transformed plant cell or the transformed plant (hereinafter, referred to as "seed of the present invention" in some cases).

A fifth invention relates to a pig edema disease vaccine including the transformant of the present invention (hereinafter, referred to as "pig edema disease vaccine of the present invention" in some cases).

A sixth invention relates to a method of controlling pig edema disease including administering the pig edema disease vaccine of the present invention to a pig (hereinafter, referred to as "method of controlling pig edema disease of the present invention" in some cases).

BRIEF DESCRIPTION OF THE DRAWINGS

FIG. 1 discloses 'HDEL' as SEQ ID NO: 14.

FIG. 2 discloses 'HDEL' as SEQ ID NO: 14.

FIG. 3 A diagram showing a designed base sequence of mStx2eB 1-4 (nucleotides 1-210 of SEQ ID NOS: 6-9, respectively, in order of appearance) compared based on CLUSTALW (http://align.genome.jp/). FIG. 3 discloses the 'Stx2eB' sequence as nucleotides 1-210 of SEQ ID NO: 5.

FIG. 4 A diagram showing a concept of synthesis of mStx2eB by PCR.

FIG. 5 A diagram showing results obtained by: developing PCR products in a 1.5% agarose gel; staining the gel with ethidium bromide; and detecting DNA bands by UV irradiation (pictures).

FIG. 7 A diagram showing constructions of Stx2eA expression vectors. In the diagram, the symbol "→" represents a translation initiation site, and the symbol "∇" represents a site to be cut after the translation. FIG. 7 discloses 'HDEL' as SEQ ID NO: 14.

FIG. 12 A diagram showing amounts of Stx2eA accumulated in protoplast of *Lactuca sativa* transformed with expression vectors of Stx2eA added with endoplasmic reticulum retention signal peptides (picture).

FIG. 17 A diagram showing a designed base sequence of mStx2eB5 (nucleotides 1-210 of SEQ ID NO: 79) compared based on CLUSTALW (http://align.genome.jp/). FIG. 17 discloses the 'Stx2eB' sequence as nucleotides 1-210 of SEQ ID NO: 5.

BEST MODE FOR CARRYING OUT THE INVENTION

Figure 1:
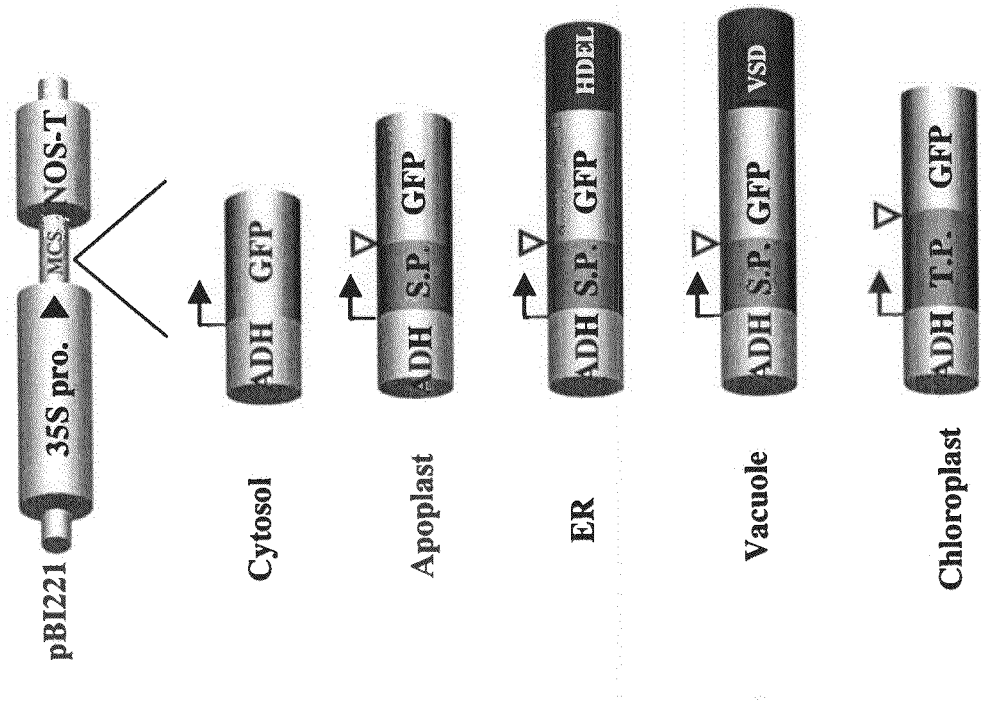
FIG. 1 A diagram showing constructions of GFP reporter expression vectors. In the diagram, the symbol "→" represents a translation initiation site, and the symbol "∇" represents a site to be cut after the translation.

A DNA construct of the present invention is characterized by including the 5'-untranslated region of an alcohol dehydrogenase gene derived from a plant and a DNA encoding an Stx2e protein added with a secretory signal peptide derived from a plant at the amino terminus and operably-linked to the region.

The 5'-untranslated region of an alcohol dehydrogenase gene is a region including a sequence between the base at the transcription initiation site of a gene encoding an alcohol dehydrogenase gene and the base before the translation initiation site (ATG, methionine). The region has an ability to increase a translation level. The "ability to increase a translation level" is an ability to increase an amount of a protein produced by translation when the information encoded in a structural gene is transcribed and, subsequently, translated to produce a protein. The region may be derived from a plant, and it is preferably derived from a plant belonging to the family Solanaceae, Brassicaceae, or Asteraceae, further preferably derived from a plant belonging to the genus *Nicotiana, Arabidopsis, Lactuca*, etc., more preferably derived from *Nicotiana tabacum, Arabidopsis thaliana, Lactuca sativa*, etc.

The 5'-untranslated region of an alcohol dehydrogenase gene is particularly preferably a region including the base sequence of SEQ ID NO: 1, e.g., the base sequence of the 5'-untranslated region of an alcohol dehydrogenase gene derived from *Nicotiana tabacum*.

The 5'-untranslated region of an alcohol dehydrogenase gene derived from a plant can be isolated from an alcohol dehydrogenase gene of a plant cultured cell where an alcohol dehydrogenase is highly expressed (see JP 2003-79372 A). Meanwhile, in the case of a region having a determined base sequence, such as the 5'-untranslated region of an alcohol dehydrogenase gene derived from *Nicotiana tabacum*, the region can be synthesized by chemical synthesis or PCR using a genomic DNA as a template and using the base sequences of the 5'- and 3'-termini of the region as primers. In addition, if part of the region having a determined base sequence is used as a probe, the 5'-untranslated region of an alcohol dehydrogenase gene derived from another plant can be searched and isolated.

The 5'-untranslated region of an alcohol dehydrogenase gene represented by the base sequence of SEQ ID NO: 1 may have substitution, deletion, insertion, or addition of one or several bases as long as the region has an ability to increase a translation level. The term "several" is a number of preferably 2 to 10, further preferably 2 to 5, particularly preferably 2 to 3.

In addition, a DNA having a identity of preferably 85% or more, particularly preferably 90% or more to the 5'-untranslated region of an alcohol dehydrogenase gene and having an ability to increase a translation level may be used.

Whether the above-mentioned region has an ability to increase a translation level or not can be confirmed by: for example, a transient assay using GUS β-glucuronidase) gene or luciferase gene as a reporter gene in *Nicotiana tabacum* cultured cells; an assay in transformed cells engineered to carry the region in a chromosome; etc.

The 5'-untranslated region of an alcohol dehydrogenase gene derived from a plant is linked to a DNA encoding an Stx2e protein added with a secretory signal peptide derived from a plant at the amino terminus so that the DNA can be expressed. The phrase "the DNA can be expressed" refers to the fact that the Stx2e protein is produced in host cells when a vector obtained by inserting the DNA construct of the present invention into a vector including a suitable promoter is introduced into suitable host cells. In addition, the term "linked" refers to a case where two DNAs are directly linked and a case where two DNAs are linked via another base sequence.

The Stx2e protein is a toxin protein of an edema disease bacterium and includes one A-subunit that is a toxin itself and five B-subunits involved in invasion into intestinal mucosa. The A-subunit is represented by the amino acid sequence of SEQ ID NO: 2, and the B-subunit is represented by the amino acid sequence of SEQ ID NO: 3.

The DNA encoding an Stx2e protein included in a DNA construct of the present invention may be a DNA encoding an Stx2e protein including both the A-subunit and the B-subunit or a DNA encoding only the A-subunit or the B-subunit. However, in the case where a DNA encoding A-subunit is included, the base sequence of the DNA is preferably modified before use so that A-subunit produced has no toxin.

In the DNA construct of the present invention, the DNA encoding an Stx2e protein is preferably a DNA encoding only B-subunit.

The Stx2e protein encoded in a DNA construct of the present invention may include substitution, deletion, insertion, or addition of one or several amino acids in the amino acid sequence of the Stx2e protein (SEQ ID NO: 2 and/or SEQ ID NO: 3) as long as the protein can cause an immune response when administered to a pig. The term "several" is, in the case of A-subunit, a number of preferably 2 to 30, further preferably 2 to 20, still further preferably 2 to 10; while the term is, in the case of B-subunit, a number of preferably 2 to 10, further preferably 2 to 5, still further preferably 2 to 3.

In addition, the protein may be a protein that has a identity of preferably 85% or more, more preferably 90% or more, particularly preferably 95% or more to the amino acid sequence of an Stx2e protein (SEQ ID NO: 2 and/or SEQ ID NO: 3) and may cause an immune response when administered to a pig.

A DNA encoding an Stx2e protein can be easily produced by a general genetic engineering technique based on the base sequences of SEQ ID NO: 4 and/or SEQ ID NO: 5. Specifically, an edema disease bacterium capable of producing an Stx2e protein is used to prepare a cDNA library in accordance with a conventional method, and a clone of interest is selected using a probe prepared based on the above-mentioned base sequences from the library, to thereby yield a DNA encoding an Stx2e protein. Moreover, the DNA can be synthesized by chemical synthesis based on the base sequence or PCR using the above-mentioned base sequences of the 5'- and 3'-termini as primers and using a genomic DNA as a template.

In the base sequence of a DNA encoding an Stx2e protein to be used for preparation of a DNA construct of the present invention, codons showing amino acid residues that constitute the Stx2e protein are preferably modified depending on host cells for producing the protein so that the translation level of the Stx2e protein is increased.

The codons can be modified with reference to the method of Kang et al. (2004), for example (the method will be described in detail in Examples). In addition, the codons can be modified by: selecting codons that are frequently used in host cells; selecting codons with high GC contents; or selecting codons that are frequently used in a housekeeping gene of host cells.

Examples of a base sequence obtained by modifying codons in the base sequence represented by SEQ ID NO: 5 include base sequences represented by SEQ ID NOS: 6 to 9 and 79. In preparation of a DNA construct of the present invention, a DNA having the base sequence represented by SEQ ID NO: 6, 8, 9, or 79 is preferably used.

Moreover, a DNA hybridizing with a DNA having any of the base sequences of SEQ ID NO: 4 and/or SEQ ID NOS: 5 to 9 under stringent conditions may be used. The term "stringent conditions" refers to conditions where a so-called specific hybrid is formed and a non-specific hybrid is not formed. Examples thereof include conditions where DNAs having high identity of, for example, preferably 80% or more, more preferably 90% or more, and particularly preferably 95% or more, hybridize with each other and DNAs having identity of less than the value do not hybridize with each other. For example, the conditions include the hybridization in 2×SSC (330 mM NaCl, 30 mM citric acid) and at 42° C.

The DNA encoding an Stx2e protein is linked to a DNA encoding a secretory signal peptide derived from a plant so that the secretory signal peptide is added to the amino terminus of the Stx2e protein. The term "added" refers to a case where the secretory signal peptide is directly linked to the amino terminus of the Stx2e protein and a case where the secretory signal peptide is linked via another peptide to the amino terminus of the Stx2e protein. In the case where a DNA encoding an Stx2e protein encodes an Stx2e protein including both the A-subunit and the B-subunit, in order to express the A-subunit and the B-subunit as a fused protein, the DNA encoding the Stx2e protein may be linked to a DNA encoding the secretory signal peptide so that the secretory signal peptide is added to the amino terminus of the fused protein, while in order to separately express the A-subunit and the B-subunit, the DNA encoding the Stx2e protein may be linked to a DNA encoding the secretory signal peptide so that the secretory signal peptide is added to the amino termini of both the A-subunit and the B-subunit.

The secretory signal peptide is preferably derived from a plant belonging to the family Solanaceae, Brassicaceae, or Asteraceae, further preferably a plant belonging to the genus *Nicotiana, Arabidopsis, Lactuca*, etc., more preferably *Nicotiana tabacum* or *Arabidopsis thaliana, Lactuca sativa*, etc.

Moreover, it is preferably derived from a β-D-glucan exohydrolase of *Nicotiana tabacum* or a 38-kDa peroxidase of *Nicotiana tabacum* (GenBank Accession D42064).

Examples of the secretory signal peptide include a peptide that is derived from a β-D-glucan exohydrolase of *Nicotiana tabacum* and has the amino acid sequence represented by SEQ ID NO: 10. The base sequence of a DNA encoding the secretory signal peptide is represented by SEQ ID NO: 11, for example.

The DNA encoding the secretory signal peptide can be searched and isolated from various plants or can be obtained from cDNAs of various plants using a probe prepared based on the base sequence of SEQ ID NO: 11 or obtained by a technique such as chemical synthesis or PCR based on the base sequence.

The DNA construct of the present invention is preferably a DNA construct in which a DNA consisting of the base sequence of SEQ ID NO: 1, a DNA consisting of the base sequence of SEQ ID NO: 11, and a DNA consisting of any of the base sequences of SEQ ID NOS: 5 to 9 are linked. Examples of the DNA construct of the present invention include a DNA construct having the base sequence of SEQ ID NO: 12.

The DNA encoding the Stx2e protein is preferably linked to a DNA encoding an endoplasmic reticulum retention signal peptide or a vacuolar transport signal peptide so that the endoplasmic reticulum retention signal peptide or vacuolar transport signal peptide is added to the carboxyl terminus of the Stx2e protein. The term "added" refers to a case where the endoplasmic reticulum retention signal peptide or vacuolar transport signal peptide is directly bonded to the carboxyl terminus of the Stx2e protein and a case where the endoplasmic reticulum retention signal peptide or vacuolar transport signal peptide is bonded via another peptide to the carboxyl terminus of the Stx2e protein. In the case where the DNA encoding an Stx2e protein encodes an Stx2e protein including both the A-subunit and the B-subunit, in order to express the A-subunit and the B-subunit as a fused protein, the DNA encoding the Stx2e protein may be linked to a DNA encoding an endoplasmic reticulum retention signal peptide or vacuolar transport signal peptide so that the endoplasmic reticulum retention signal peptide or vacuolar transport signal peptide is added to the carboxyl terminus of the fused protein, while in order to separately express the A-subunit and the B-subunit, the DNA encoding the Stx2e protein may be linked to a DNA encoding an endoplasmic reticulum retention signal peptide or vacuolar transport signal peptide so that the endoplasmic reticulum retention signal peptide or vacuolar transport signal peptide is added to the carboxyl termini of both or one of the A-subunit and the B-subunit.

Examples of the endoplasmic reticulum retention signal peptide include an endoplasmic reticulum retention signal peptide including KDEL sequence (SEQ ID NO: 13), HDEL sequence (SEQ ID NO: 14), KDEF sequence (SEQ ID NO: 15), or HDEF sequence (SEQ ID NO: 16). For example, the endoplasmic reticulum retention signal peptide including the HDEL sequence (SEQ ID NO: 14) is preferably an endoplasmic reticulum retention signal peptide represented by the amino acid sequence of SEQ ID NO: 17, or the like. Note that the base sequence of a DNA encoding the endoplasmic reticulum retention signal peptide is represented by SEQ ID NO: 18, for example.

The vacuolar transport signal peptide is derived from preferably a plant belonging to the family Solanaceae, Brassicaceae, or Asteraceae, further preferably a plant belonging to the genus *Nicotiana, Arabidopsis, Armoraci*, etc., more preferably *Nicotiana tabacum, Arabidopsis thaliana, Armoracia rusticana*, etc. In addition, the peptide is preferably derived from a chitinase. The amino acid sequence of a vacuolar transport signal peptide derived form a *Nicotiana tabacum* chitinase is represented by SEQ ID NO: 19. Meanwhile, the base sequence of a DNA encoding a vacuolar transport signal peptide derived form a *Nicotiana tabacum* chitinase is represented by SEQ ID NO: 20, for example.

Moreover, the peptide is preferably derived from a horseradish peroxidase C1a isozyme. The amino acid sequence of a vacuolar transport signal peptide derived form a horseradish peroxidase C1a isozyme is represented by SEQ ID NO: 21. Meanwhile, the base sequence of a DNA encoding a vacuolar transport signal peptide derived form a horseradish peroxidase C1a isozyme is represented by SEQ ID NO: 22.

The DNA construct of the present invention is preferably a DNA construct including the 5'-untranslated region of an alcohol dehydrogenase gene derived from a plant, a DNA encoding an Stx2e protein including a secretory signal peptide added at the amino terminus and an endoplasmic reticulum retention signal peptide or including a vacuolar transport signal peptide added at the carboxyl terminus. In the DNA construct, a DNA consisting of base sequence of SEQ ID NO: 1, a DNA consisting of the base sequence of SEQ ID NO: 11, a DNA consisting of any of the base sequences of SEQ ID NOS: 5 to 9, and a DNA consisting of the base sequence of SEQ ID NO: 18 or 20 are linked. Examples of the DNA construct of the present invention added with an endoplasmic reticulum retention signal peptide include a DNA construct having any of the base sequences of SEQ ID NOS: 23, 75, 77, 78, and 86. Examples of the DNA construct of the present invention added with a vacuolar transport signal peptide include a DNA construct having the base sequences of SEQ ID NO: 24.

The DNA construct of the present invention can be prepared by a general genetic engineering technique, which includes the following procedures: digesting DNAs including the 5'-untranslated region of an alcohol dehydrogenase gene derived from a plant, a DNA encoding a secretory signal peptide derived from a plant, and a DNA encoding an Stx2e protein, and optionally a DNA encoding an endoplasmic reticulum retention signal peptide or a vacuolar transport signal peptide with suitable restriction enzymes; and ligating the resultant fragments with a suitable ligase.

The recombinant vector of the present invention is characterized by including the DNA construct of the present invention. The recombinant vector of the present invention may be a vector obtained by inserting a DNA encoding an Stx2e protein added with a secretory signal peptide derived from a plant at the N-terminus into a vector so that the DNA can be expressed in host cells to be introduced with the vector. The vector is not particularly limited as long as it can replicate in host cells, and examples thereof include a plasmid DNA and a viral DNA. In addition, the vector preferably includes a selective marker such as a drug resistance gene. The plasmid DNA can be prepared from *Escherichia coli* or *Agrobacterium* by the alkaline extraction method (Birnboim, H. C. & Doly, J. (1979) Nucleic acid Res 7: 1513) or a modified method thereof. Commercially available plasmids such as pBI221, pBI121, pBI101, and pIG121Hm may be used. The viral DNA may be, for example, pTB2 (Donson et al., 1991) (see Donson J., Kerney C M., Hilf M E., Dawson W O. Systemic expression of a bacterial gene by a tobacco mosaic virus-based vector. Proc. Natl. Acad. Sci. (1991) 88: 7204-7208).

Promoters to be used in vectors may be appropriately selected depending on host cells to be introduced with vectors. The promoters are preferably a cauliflower mosaic virus 35S promoter (Odell et al., 1985, Nature 313:810), a rice actin promoter (Zhang et al. 1991 Plant Cell 3:1155), a corn ubiquitin promoter (Cornejo et al., 1993, Plant Mol. Biol., 23:567), etc. for example. Meanwhile, terminators to be used in vectors may be appropriately selected depending on host cells to be introduced with vectors. The terminators are preferably a nopaline synthase gene transcription terminator, a cauliflower mosaic virus 35S terminator, etc.

The recombinant vector of the present invention may be prepared as follows.

First, a DNA construct of the present invention is digested with a suitable restriction enzyme, or a restriction enzyme site is added to the DNA construct by PCR. Subsequently, the DNA construct is inserted into the restriction enzyme site or multicloning site of a vector.

The transformant of the present invention is characterized by being transformed with the recombinant vector of the present invention. The host cells to be used for transformation may be eukaryotic cells or prokaryotic cells.

The eukaryotic cells are preferably plant cells, particularly preferably cells of plants belonging to the family Asteraceae, Solanaceae, Brassicaceae, and Chenopodiaceae. Moreover, the eukaryotic cells are preferably cells of plants belonging to the genus *Lactuca*, particularly preferably *Lactuca sativa* cells. In the case of using *Lactuca sativa* cells as host cells, a cauliflower mosaic virus 35S RNA promoter or the like may be used.

The prokaryotic cells may be cells of *Escherichia coli*, *Agrobacterium tumefaciens*, etc.

The transformant of the present invention can be prepared by a general genetic engineering technique by introducing a vector of the present invention into host cells. For example, the transformant can be prepared by the introduction method using *Agrobacterium* (Hood, et al., 1993, Transgenic, Res. 2:218, Hiei, et al., 1994 Plant J. 6:271), an electroporation method (Tada, et al., 1990, Theor. Appl. Genet, 80:475), a polyethylene glycol method (Lazzeri, et al., 1991, Theor. Appl. Genet. 81:437), a particle gun method (Sanford, et al., 1987, J. Part. Sci. tech. 5:27), a polycation method (Ohtsuki), etc.

After introduction of the vector of the present invention into host cells, a transformant of the present invention can be selected based on the phenotype of a selective marker. If the selected transformant is cultured, the Stx2e protein can be produced. The culture medium and conditions for culture may be suitably selected depending on the type of a transformant.

In addition, in the case of using a plant cell as a host cell, culture of selected plant cell in accordance with a conventional method can regenerate a plant and accumulate the Stx2e protein in the plant cells or outside the cell membranes of the plant cells. The method depends on the type of the plant cell, and examples thereof include the method of Visser et al. (Theor. Appl. Genet, 78:594 (1989)) for potato and the method of Nagata and Takebe (Planta, 99:12 (1971)) for *Nicotiana tabacum*.

In the case of *Lactuca sativa*, a shoot can be regenerated in MS medium containing 0.1 mg/l NAA (naphthalene acetic acid), 0.05 mg/l BA (benzyladenine), and 0.5 g/l polyvinylpyrrolidone, and culture of the regenerated shoot in a ½ MS medium containing 0.5 g/l polyvinylpyrrolidone may cause rooting.

The seed of the present invention can be obtained by collecting a seed from a plant regenerated as above. If the seed of the present invention are sown and cultivated by a suitable method, a plant capable of producing an Stx2e protein can be obtained and is included in the transformant of the present invention.

The pig edema disease vaccine of the present invention is characterized by including a transformant of the present invention. The pig edema disease vaccine of the present invention may include the entire or part of the transformant containing an Stx2e protein of the present invention. Moreover, the transformant may be used without further treatments, or the transformant may be dried or pulverized before use. In addition, the pig edema disease vaccine of the present invention may contain an adjuvant capable of increasing the immunogenicity of the Stx2e protein.

In general, in view of safety, aluminum hydroxide or the like is used as an adjuvant. Meanwhile, a B-subunit itself of an Stx2e protein has an adjuvant activity, and therefore, in the case where a DNA construct of the present invention includes a DNA encoding a B-subunit, high immunogenicity can be achieved unless an adjuvant is further added.

The method of controlling pig edema disease of the present invention is characterized by including administering the pig edema disease vaccine of the present invention to a pig. Immunization with the pig edema disease vaccine of the present invention is preferably performed for baby pigs having a higher incidence of edema disease. Examples of the immunization method include: a method including administrating the pig edema disease vaccine of the present invention to a mother pig to give an antibody produced by the mother pig to a baby pig via milk; and a method including administering the pig edema disease vaccine of the present invention to a baby pig to directly immunize the baby pig.

Examples of the method of administering the pig edema disease vaccine of the present invention to a pig include: a method including administering a mixture of a pig feed with the pig edema disease vaccine of the present invention to a pig; and a method including nasally administering the vaccine to a pig. In this case, the dose of the vaccine is preferably 4 mg per day or more, more preferably 16 mg per day or more based on the mass of the Stx2e protein. The pig edema disease vaccine is preferably administered multiple times at a certain interval. For example, the vaccine is administered every 4 to 7 days twice or three times in total.

EXAMPLES

(1) Construction of GFP Expression Vector

In order to study control of protein localization in *Lactuca sativa* cells, expression vectors including a DNA encoding a green fluorescent protein (GFP) including each signal peptide added were prepared as follows (FIG. 1).

The 5'-untranslated region of an alcohol dehydrogenase gene derived from *Nicotiana tabacum* (NtADH 5'UTR, SEQ ID NO: 1) was amplified by PCR using ADH-221 (Sato et. al., 2004) as a template and using ADH XbaI-F primer (SEQ ID NO: 25) and ADH NsiI-R primer (SEQ ID NO: 26). The DNA region encoding a signal peptide of β-D glucan exohydrolase (GenBank ACCESSION AB017502) (SEQ ID NO: 11) was amplified using a genomic DNA of *Nicotiana tabacum* as a template and using PD NsiI-F primer (SEQ ID NO:27) and βD EcoRI-R primer (SEQ ID NO:28). The resultant DNA fragments of the NtADH 5'UTR and signal peptide were treated with NsiI (manufactured by TOYOBO CO., LTD.), and ligation was performed using ligation high (manufactured by TOYOBO CO., LTD.), followed by blunting to clone the fragments into the EcoRV gap of pBluescript II SK (manufactured by Stratagene) (plasmid 1).

Plasmid 1 was treated with NsiI, and the termini were blunted with T4 DNA polymerase (manufactured by TOYOBO CO., LTD.), followed by self-ligation to perform fusion so that the initiation codon of NtADH (atg) corresponds to the initiation codon of beta-D glucan exohydrolase (plasmid 2). A DNA encoding GFP having a vacuolar transport signal peptide (SEQ ID NO: 19) at the C-terminus (pSGFP5T, Di Sansebastiano et al., 1998) was inserted into plasmid 2 via the EcoRI site (vacuole-type GFP)

PCR was performed using pSGFP5T as a template and using GFP-F primer (SEQ ID NO: 29) and GFP-R primer (SEQ ID NO: 30). The termini of the resultant DNA fragments were blunted and cloned into the EcoRV gap of pBluescript II SK (plasmid 3). GFP fragments were digested from plasmid 3 with EcoRI and XhoI and inserted into the EcoRI-XhoI gap of plasmid 2 (apoplast-type GFP).

GFP fragments were digested from plasmid 3 with NsiI and XhoI and inserted into the NsiI-EcoRI gap of plasmid 1 (cytosol-type GFP).

PCR was performed using pSGFP5 as a template and using GFP-F primer and GFP HDEL-R primer (SEQ ID NO: 31) ('HDEL' disclosed as SEQ ID NO: 14). The termini of the resultant DNA fragments were blunted and cloned into the EcoRV gap of pBluescript II SK (plasmid 4). GFP fragments were digested from plasmid 4 with EcoRI and XhoI and inserted into the EcoRI-XhoI gap of plasmid 2 (endoplasmic reticulum-type GFP).

A DNA fragment encoding a chloroplast transport signal peptide derived from *Lactuca sativa* Rbcs (Rubisco small subunit) (GenBank ACCESSION D14001) (transit peptide, T.P., SEQ ID NO: 45) was amplified by PCR using cDNA of a leaf of *Lactuca sativa* as a template and using TP NsiI-F primer (SEQ ID NO: 32) and TP EcoRI-R primer (SEQ ID NO: 33). The resultant fragments were treated with NsiI and EcoRI and ligated to the NsiI-EcoRI gap of plasmid 1 (plasmid 5). Plasmid 5 was treated with NsiI, and the termini were blunted with T4 DNA polymerase (manufactured by TOYOBO CO., LTD.), followed by self-ligation to perform fusion so that the initiation codon of NtADH corresponds to the initiation codon of Rbcs (plasmid 6). GFP fragments were digested from plasmid 3 with EcoRI and XhoI and inserted into the EcoRI-XhoI gap of plasmid 6 (chloroplast-type GFP).

Those GFP expression vectors can be constructed with reference to the following documents.

Di Sansebastiano et. al., Specific accumulation of GFP in a non-acidic vacuolar compartment via a C-terminal propeptide-mediated sorting pathway. Plant J. (1998) 15, 449-457

Satoh et al., The 5'-untranslated region of the tobacco alcohol dehydrogenase gene functions as an effective translational enhancer in plant. J. Biosci. Bioeng. (2004) 98,1-8

The above-mentioned localized-type GFPs were inserted as follows into the multicloning site (MCS) of a transient expression vector in plant cells, pBI221 (Clontech).

In order to introduce SalI, KpnI, and SmaI sites into the MCS, SalKpnSma-F (SEQ ID NO: 34) and SalKpnSma-R (SEQ ID NO: 35) were annealed and phosphorylated with T4 polynucleotide kinase (T4 PNK) (TaKaRa) and inserted into the SacI gap of pBI221 (plasmid 7). The localized-type GFPs were inserted into plasmid 7 using XbaI and KpnI, and the resultant product was arranged between a cauliflower mosaic virus 35S RNA promoter (35S pro.) and a nopaline synthase gene transcription terminator (NOS-T), to thereby prepare a GFP expression vector.

(2) Construction of Stx2eB Expression Vector

Vectors including a DNA construct of the present invention that includes a DNA encoding a B-subunit of an Stx2e protein (Stx2eB) (SEQ ID NO: 5) added with each signal peptide were prepared as follows.

PCR was performed using Kozak-stx2eb-F primer (SEQ ID NO: 36) and stx2eb-R primer (SEQ ID NO: 37) to amplify a DNA fragment encoding the mature region of an Stx2eB (excluding secretory signal peptides to periplasm, Ala19 to Asn87). The resultant DNA fragment was cloned into the EcoRV gap of pBluescript II SK. The resultant plasmid was digested with HindIII and treated with T4 DNA polymerase, and self-ligation was performed to convert the HindIII site into the NheI site (plasmid 8).

Kozak-Stx2eB fragment was digested from plasmid 8 with XbaI and KpnI and inserted into the XbaI-KpnI gap of plasmid 7, to thereby prepare a Kozak-ligated cytosol-type Stx2eB expression vector (Kozak-Cytosol-Stx2eB) (plasmid 9).

NtADH 5'UTR fragment was amplified using ADH XbaI-F and ADH BamHI-R primer (SEQ ID NO: 38). The resultant DNA fragment was treated with XbaI and BamHI inserted into the XbaI-BamHI gap of plasmid 9, to thereby prepare an NtADH 5'-UTR-ligated cytosol-type Stx2eB expression vector (ADH-Cytosol-Stx2eB) (plasmid 10).

PCR was performed using plasmid 2 as a template and using βD-Kozak-F primer (SEQ ID NO: 39) and βD BamHI-R primer (SEQ ID NO: 40) to amplify DNA encoding a secretory signal peptide. The resultant DNA fragment was treated with XbaI and BamHI and inserted into the XbaI-BamHI gap of plasmid 9 (plasmid 11) (Kozak-Apoplast-Stx2eB).

In order to add an endoplasmic reticulum retention signal, HDEL-F primer (SEQ ID NO: 41) ('HDEL' disclosed as SEQ ID NO: 14) and HDEL-R primer (SEQ ID NO: 42) ('HDEL' disclosed as SEQ ID NO: 14) were annealed and phosphorylated with T4 PNK, and the resultant product was inserted into the BglII gap of plasmid 11, which had been dephosphorylated with alkaline phosphatase (AP) (TaKaRa), to thereby prepare a Kozak-ligated endoplasmic reticulum-type Stx2eB expression vector (Kozak-ER-Stx2eB) (plasmid 12).

In order to prepare a DNA fragment obtained by fusing NtADH 5'UTR and DNA encoding a secretory signal peptide, PCR was performed using plasmid 2 as a template and using ADH XbaI-F primer and βD BamHI-R primer. The resultant DNA fragment was treated with XbaI and BamHI and inserted into the XbaI-BamHI gap of plasmid 9, to thereby prepare an NtADH 5'-ligated apoplast-type Stx2eB expression vector (ADH-Apoplast-Stx2eB) (plasmid 13).

In order to add an endoplasmic reticulum retention signal, an HDEL-F primer ('HDEL' disclosed as SEQ ID NO: 14) and an HDEL-R primer ('HDEL' disclosed as SEQ ID NO: 14) were annealed and phosphorylated with T4 PNK, and the resultant product was inserted into the BglII gap of plasmid 13, which had been dephosphorylated with AP, to thereby prepare an NtADH 5'-UTR-ligated endoplasmic reticulum-type Stx2eB expression vector (ADH-ER-Stx2eB) (plasmid 14).

In order to add an vacuolar transport signal, VSD-F primer (SEQ ID NO: 43) and VSD-R primer (SEQ ID NO: 44) were annealed and phosphorylated with T4 PNK, and the resultant product was inserted into the BglII gap of plasmid 13, which had been dephosphorylated with AP, to thereby prepare an NtADH 5'-UTR-ligated vacuole-type Stx2eB expression vector (ADH-Vacuole-Stx2eB) (plasmid 15).

In order to add a chloroplast transport signal peptide (SEQ ID NO: 45), PCR was performed using plasmid 6 as a template and using ADH XbaI-F primer and TP BamHI-R primer (SEQ ID NO: 46). The resultant DNA fragment was treated with XbaI and BamHI and inserted into the XbaI-BamHI gap of plasmid 9, to thereby prepare an NtADH 5'-UTR-ligated chloroplast-type Stx2eB expression vector (ADH-Chloroplast-Stx2eB) (plasmid 16).

Figure 2:
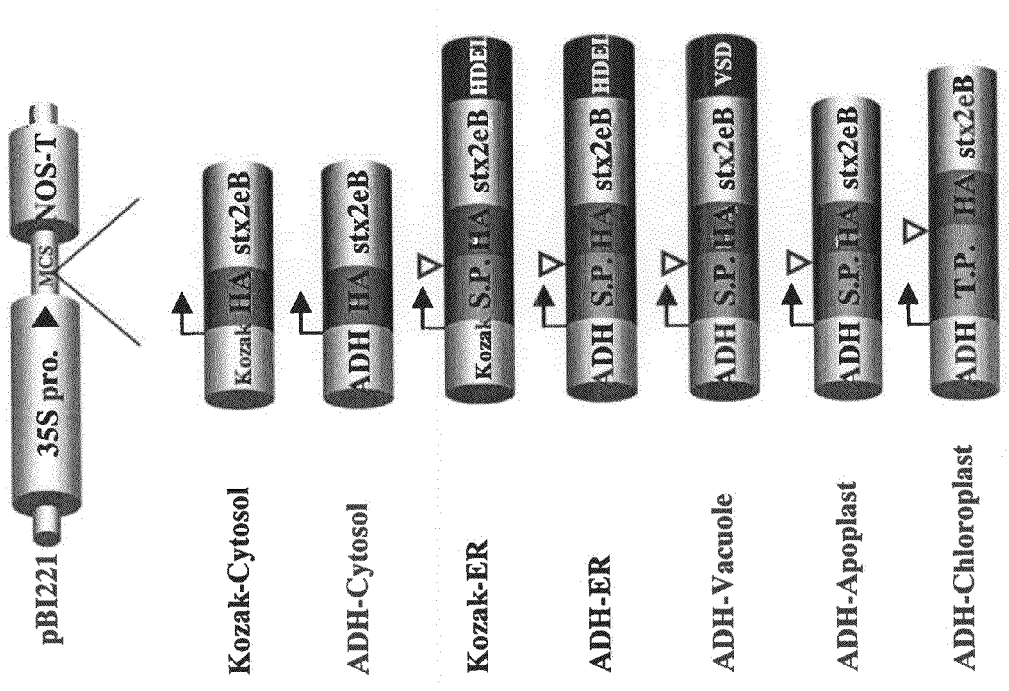
FIG. 2 A diagram showing constructions of Stx2eB expression vectors. In the diagram, the symbol "→" represents a translation initiation site, and the symbol "∇" represents a site to be cut after the translation.
Figure 6:
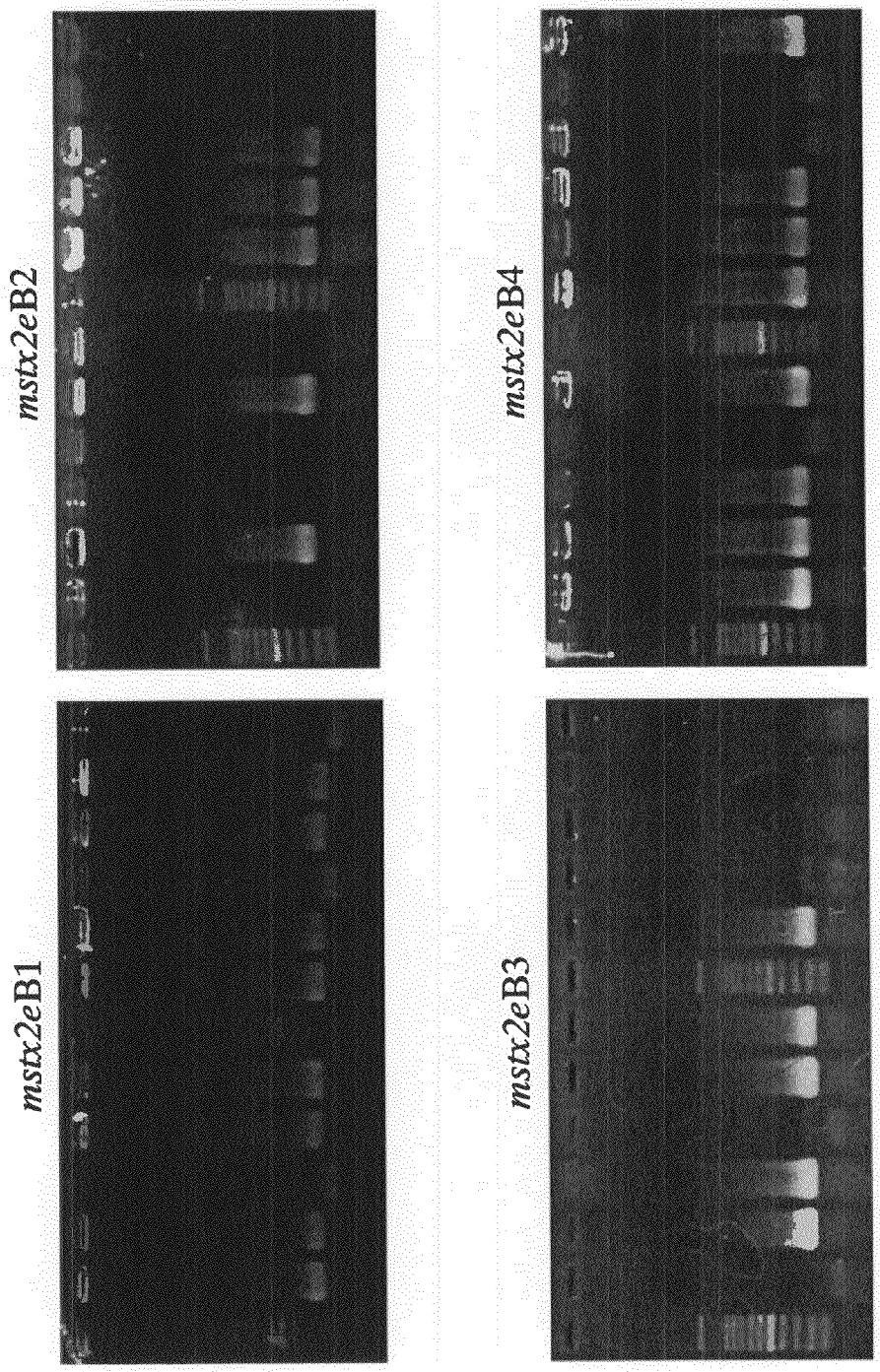
FIG. 6 A diagram showing results obtained by: developing a solution obtained after direct PCR in a 1.5% agarose gel; staining the gel with ethidium bromide; and detecting DNA bands by UV irradiation (pictures).

HA tag was fused as a peptide tag for detecting an Stx2eB. In order to add HA tag, HA-F primer (SEQ ID NO: 47) and HA-R primer (SEQ ID NO: 48) were annealed and phosphorylated with T4 PNK. The resultant phosphorylated HA fragment was inserted into the BamHI gaps of plasmids 9, 10, 12, 13, 14, 15, and 16, to thereby prepare Stx2eB expression vectors: Kozak-Cytosol-Stx2eB, ADH-Cytosol-Stx2eB, Kozak-ER-Stx2eB, ADH-Apoplast-Stx2eB, ADH-ER-Stx2eB, ADH-Vacuole-Stx2eB, and ADH-Chloroplast-Stx2eB, which were used in the following expression tests (FIG. 2).

(3) Construction of Codon-Modified Stx2eB Expression Vector

The codons in the base sequence of a DNA encoding Stx2eB represented by SEQ ID NO: 5 were modified by the following method to prepare endoplasmic reticulum codon-modified DNAs encoding Stx2eBs added with NtADH 5'UTR.

(a) Design of Codon-Modified Stx2eB

The following four sequences were designed as codon-modified Stx2eB's: 1) a sequence based on the method of Kang et al. (2004); 2) a sequence including selected codons that are frequently used in *Lactuca sativa*; 3) a sequence including selected codons that have high GC contents and are frequently used in *Lactuca sativa*; and 4) a sequence including selected codons that are frequently used in housekeeping genes (actin gene, β-tubulin gene).

1) Sequence Based on the Method of Kang et al. (2004)

A codon modification flowchart was created based on the LTB gene sequences before and after modification and *Nicotiana tabacum* codon usage table described in the document, and codons of an Stx2eB were modified based on the flowchart and *Lactuca sativa* codon usage table. The resultant codon-modified Stx2eB was designated as mStx2eB1 (SEQ ID NO: 6). The *Lactuca sativa* codon usage table used is the codon usage of *Lactuca sativa* on the database of Kazusa DNA Research Institute (http://www.kazusa.or.jp/codon/index.html).

2) Sequence Including Selected Codons that are Frequently Used in *Lactuca sativa*

Codon modification was performed based on the *Lactuca sativa* codon usage table using only the codon that is the most frequently used. For example, among codons of Ala, the codon that is the most frequently used is GCA. Therefore, all Ala codons in Stx2eB were converted into GCA. The resultant codon-modified Stx2eB was designated as mStx2eB2 (SEQ ID NO: 7).

3) Sequence Including Selected Codons that have High GC Contents and are Frequently Used in *Lactuca sativa*

A codon that has a high GC content and is frequently used in *Lactuca sativa* was selected based on the *Lactuca sativa* codon usage table, and codon modification was performed. For example, among codons of Ala, codons having the highest GC content are GCC and GCG, and a codon that is frequently used is GCC. Therefore, all Ala codons in Stx2eB were converted into GCC. The resultant codon-modified Stx2eB was designated mStx2eB3 (SEQ ID NO: 8).

4) Sequence Including Selected Codons that are Frequently Used in Housekeeping Genes (Actin Gene, β-Tubulin Gene)

A codon that is frequently used in *Lactuca sativa* housekeeping genes was selected, and codon modification was performed. Actin and β-tubulin 1, 2, 3 were selected as the *Lactuca sativa* housekeeping genes. The base sequences of the genes were based on the NCBI (http://www.ncbi.nlm.nih.gov/). Codons used in the genes and codon usages are collectively shown in Tables 1 and 2. Among the codons, the codon that is the most frequently used was selected, and codon modification was performed. The resultant codon-modified Stx2eB was designated as mStx2eB4 (SEQ ID NO: 9).

TABLE 1

| Amino acid | Triplet | Codon usage | Actin | β-tubulin 1 | 2 | 3 | Optimization |
|---|---|---|---|---|---|---|---|
| Ala | GCA | 0.35 | 3 | 4 | 3 | 5 | |
| | GCC | 0.20 | 3 | 7 | 5 | 6 | GCC |
| | GCG | 0.11 | 1 | 1 | 1 | 0 | |
| | GCT | 0.34 | 5 | 4 | 7 | 4 | |
| Arg | AGA | 0.39 | 4 | 1 | 3 | 4 | |
| | AGG | 0.22 | 1 | 6 | 3 | 4 | |
| | CGA | 0.13 | 0 | 1 | 1 | 0 | |
| | CGC | 0.06 | 0 | 3 | 0 | 2 | |
| | CGG | 0.07 | 0 | 0 | 1 | 0 | |
| | CGT | 0.14 | 3 | 4 | 7 | 5 | CGT |
| Asn | AAC | 0.46 | 3 | 8 | 8 | 7 | AAC |
| | AAT | 0.54 | 2 | 6 | 6 | 7 | |
| | | | 0 | | | | |
| Asp | GAC | 0.31 | 1 | 5 | 7 | 4 | |
| | GAT | 0.69 | 5 | 7 | 5 | 8 | GAT |
| Cys | TGC | 0.42 | 0 | 5 | 4 | 5 | TGC |
| | TGT | 0.58 | 0 | 4 | 5 | 4 | |
| Gln | CAA | 0.71 | 2 | 7 | 9 | 9 | CAA |
| | CAG | 0.29 | 2 | 5 | 3 | 3 | |
| Gly | GGA | 0.33 | 2 | 7 | 4 | 7 | |
| | GGC | 0.14 | 1 | 3 | 0 | 1 | |
| | GGG | 0.20 | 1 | 4 | 6 | 4 | |
| | GGT | 0.34 | 5 | 4 | 8 | 6 | GGT |
| His | CAC | 0.36 | 3 | 2 | 3 | 1 | |
| | CAT | 0.64 | 2 | 4 | 3 | 5 | CAT |
| Ile | ATA | 0.27 | 0 | 0 | 0 | 1 | |
| | ATC | 0.30 | 2 | 5 | 6 | 6 | ATC |
| | ATT | 0.44 | 5 | 5 | 4 | 3 | |
| Leu | CTA | 0.12 | 0 | 4 | 7 | 2 | |
| | CTC | 0.14 | 4 | 9 | 8 | 8 | CTC |

TABLE 1-continued

|  |  | β-tubulin | | | | |
| --- | --- | --- | --- | --- | --- | --- |
| Amino acid | Triplet | Codon usage | Actin | 1 | 2 | 3 | Optimization |
|  | CTG | 0.08 | 0 | 2 | 3 | 3 |
|  | CTT | 0.26 | 3 | 4 | 4 | 6 |
|  | TTA | 0.16 | 1 | 2 | 2 | 1 |
|  | TTG | 0.25 | 0 | 4 | 1 | 4 |
| Lys | AAA | 0.52 | 2 | 5 | 4 | 7 |
|  | AAG | 0.48 | 3 | 7 | 8 | 5 | AAG |
| Met | ATG | 1.00 | 6 | 16 | 16 | 16 | ATG |
| Phe | TTC | 0.49 | 2 | 8 | 7 | 10 | TTC |
|  | TTT | 0.51 | 3 | 8 | 9 | 6 |

TABLE 2

|  |  |  | β-tublin | | | | |
| --- | --- | --- | --- | --- | --- | --- | --- |
| Amino acid | Codon usage | Triplet | Actin | 1 | 2 | 3 | Optimization |
| Pro | CCA | 0.39 | 3 | 6 | 8 | 5 | CCA |
|  | CCC | 0.16 | 1 | 3 | 2 | 3 |
|  | CCG | 0.11 | 0 | 0 | 0 | 2 |
|  | CCT | 0.34 | 5 | 5 | 4 | 4 |
| Ser | AGC | 0.12 | 1 | 2 | 2 | 2 |
|  | AGT | 0.18 | 2 | 1 | 1 | 1 |
|  | TCA | 0.22 | 0 | 3 | 8 | 4 |
|  | TCC | 0.16 | 2 | 8 | 2 | 8 | TCC |
|  | TCG | 0.08 | 0 | 2 | 0 | 1 |
|  | TCT | 0.24 | 0 | 6 | 9 | 7 |
| Thr | ACA | 0.37 | 1 | 7 | 5 | 6 |
|  | ACC | 0.26 | 2 | 5 | 6 | 6 |
|  | ACG | 0.10 | 0 | 1 | 0 | 0 |
|  | ACT | 0.27 | 4 | 8 | 10 | 8 | ACT |
|  | ACW | — | — | — | — | 1 |
| Trp | TGG | 1.00 | 2 | 3 | 3 | 3 | TGG |
| Tyr | TAC | 0.44 | 1 | 6 | 5 | 7 | TAC |
|  | TAT | 0.56 | 4 | 2 | 3 | 1 |
| Val | GTA | 0.16 | 1 | 1 | 0 | 1 |
|  | GTC | 0.17 | 0 | 5 | 8 | 6 |
|  | GTG | 0.28 | 4 | 5 | 5 | 4 |
|  | GTT | 0.39 | 6 | 7 | 5 | 7 | GTT |
| X | CYC | — | — | — | — | 1 |

The designed base sequences of mStx2eB 1-4 were compared based on the CLUSTALW (http://align.genome.jp/) (FIG. 3).

The sequence XXG/C(X: any base) ratios and GC ratios of Stx2eB before and after codon modification are shown in Table 3. The XXG/C ratios for the proteins other than mStx2eB2 were found to be higher than the ratio for Stx2eB, and the ratio for mStx2eB3 was found to be 100%. Similarly, the GC ratios for those proteins other than mStx2eB2 were found to be higher than the ratio for Stx2eB, and the GC ratio for mStx2eB3 was the highest (61.4%).

TABLE 3

| | XXG/C (%) | GC (%) |
|---|---|---|
| Stx2eB | 47.1 | 42.4 |
| mStx2eB1 | 67.1 | 49.0 |
| mStx2eB2 | 5.7 | 30 |
| mStx2eB3 | 100 | 61.4 |
| mStx2eB4 | 60 | 49.0 |

(b) Preparation of Codon-Modified Stx2eB

Based on the base sequences of mStx2eB 1-4, primers each having six base sequences were prepared.

1) Sequence Based on the Method of Kang et al. (2004)

A: SEQ ID NO: 49

B: SEQ ID NO: 50

C: SEQ ID NO: 51

D: SEQ ID NO: 52

E: SEQ ID NO: 53

F: SEQ ID NO: 54

2) Sequence Including Selected Codons that are Frequently Used in *Lactuca sativa*

A: SEQ ID NO: 55

B: SEQ ID NO: 56

C: SEQ ID NO: 57

D: SEQ ID NO: 58

E: SEQ ID NO: 59

F: SEQ ID NO: 60

3) Sequence Including Selected Codons that have High GC Contents and are Frequently Used in *Lactuca sativa*

A: SEQ ID NO: 61

B: SEQ ID NO: 62

C: SEQ ID NO: 63

D: SEQ ID NO: 64

E: SEQ ID NO: 65

F: SEQ ID NO: 66

4) Sequence Including Selected Codons that are Frequently Used in Housekeeping Genes

A: SEQ ID NO: 67

B: SEQ ID NO: 68

C: SEQ ID NO: 69

D: SEQ ID NO: 70

E: SEQ ID NO: 71

F: SEQ ID NO: 72

The 1st PCR was performed using the oligomers synthesized above based on the method of Kang et al. (2004) under the following conditions to synthesize four codon-modified Stx2eB's. That is, PCR was performed using primers A and B, primers C and D, and primers E and F in combination to synthesize gene fragments of 87 bp (A+B), 78 bp (C+D), and 69 bp (E+F), respectively. Subsequently, the 2nd PCR was performed using A+B and C+D in combination to synthesize a gene fragment of 153 bp (A+B+C+D). Finally, the 3rd PCR was performed using A+B+C+D and E+F in combination to synthesize a gene of 210 bp (see FIG. 4). The reaction conditions are as follows: 10 μmol of an oligonucleotide, 0.2 mM of dNTP, pfu DNA polymerase buffer, and 0.3 U of pfu DNA polymerase were added with a final volume of 25 μl, and heating was performed at 94° C. for 5 minutes, and a heating treatment was performed in 25 or 30 cycles at 94° C. for 1 minute, at 56° C. or 60° C. for 1 minute, and at 72° C. for 1 minute, followed by heating at 72° C. for 5 minutes. For the 2nd PCR and 3rd PCR, 1 μl of a reaction solution after the 1st PCR and 2nd PCR was used as templates. In the 1st PCR and 2nd PCR, a target DNA was amplified, while in the 3rd PCR, a DNA having a desired size was not amplified. However, in the case of PCR using Ex Taq and using the 3rd PCR product as a template, amplified products were detected at the position of about 210 bp (FIG. 5). TA cloning for the amplified products was performed, and the presence or absence of inserts was confirmed by direct PCR (FIG. 6), followed by sequencing for the products which had been confirmed to have the inserts. As a result, it was confirmed that mStx2eB 1-4 of interest were produced.

(c) Construction of Codon-Modified Stx2eB Expression Vector

A transient expression vector for evaluating the translation levels of the codon-modified Stx2eB 1-4 was constructed. The above-mentioned vector pBI221 including a cauliflower mosaic virus 35S promoter, the 5'-untranslated region of an alcohol dehydrogenase gene derived from *Nicotiana tabacum*, and DNA encoding a signal peptide, an endoplasmic reticulum retention signal and HA tag added was digested with a restriction enzyme, and DNA fragments of interest were ligated using a DNA Ligation Kit (Mighty Mix) (TaKaRa), to thereby prepare an endoplasmic reticulum codon-modified Stx2eB expression vector (ADH-ER-mStx2eB 1-4) added with NtADH5'UTR added.

(4) Construction of Stx2eA Expression Vector

A DNA encoding the mature region of an A-subunit of an Stx2e protein (excluding a secretory signal peptide region which signals to the periplasm, Gln23 to Glu319) (Stx2eA) (SEQ ID NO: 4) added with an endoplasmic reticulum retention signal peptide was prepared by the following method.

Figure 7:
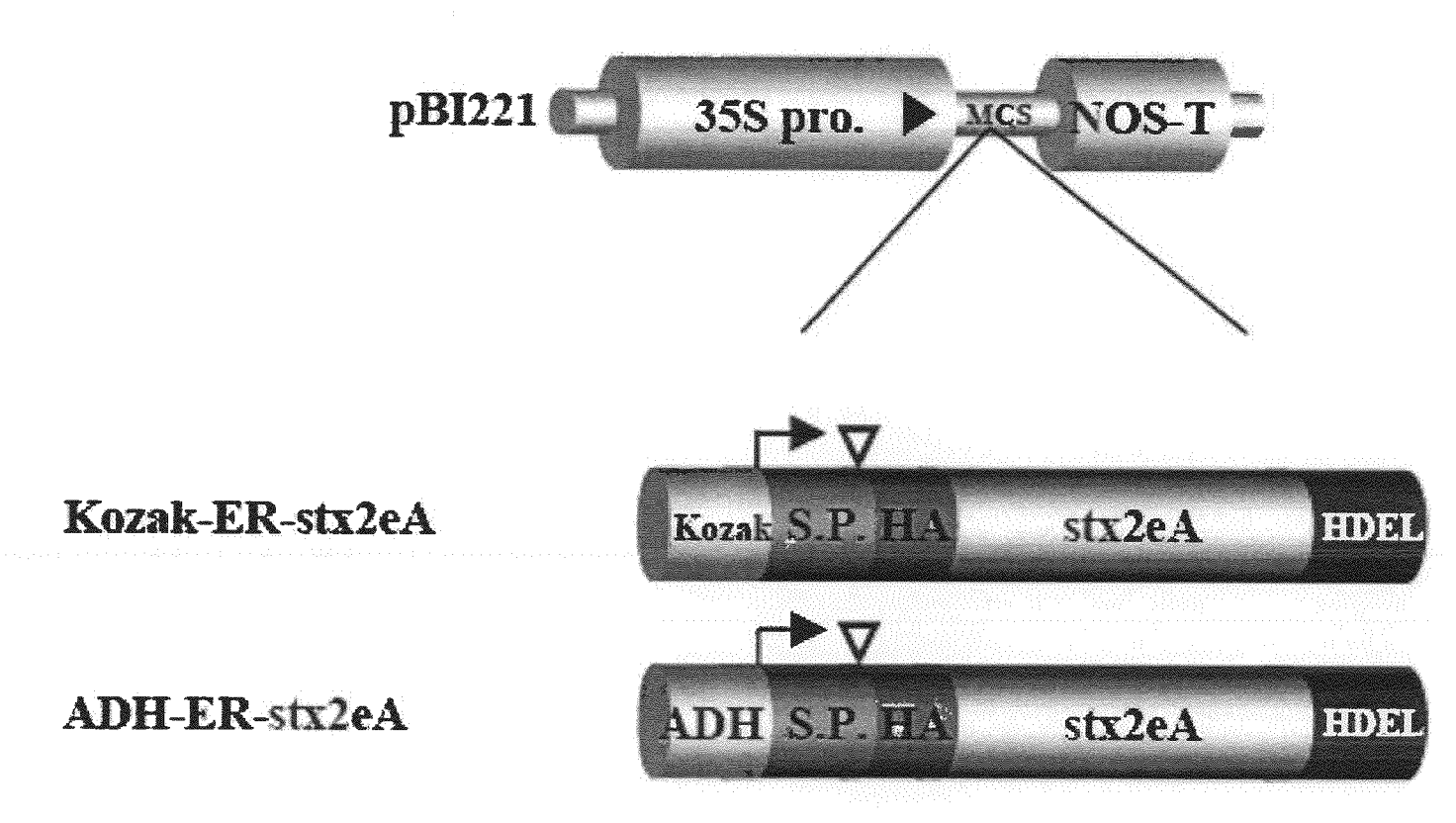

PCR was performed using Stx2eA BamHI-F primer (SEQ ID NO: 73) and Stx2eA BglII-R primer (SEQ ID NO: 74). The resultant DNA fragment was treated with BamHI and BglII and inserted into the BamHI-BglII gaps of the above-mentioned expression vectors, Kozak-ER-Stx2eB and ADH-ER-Stx2eB, to thereby prepare Kozak-ER-Stx2eA or ADH-ER-Stx2eA (FIG. 7).

(5) Transient Expression Test Using *Lactuca sativa* Protoplast

A leaf of potted *Lactuca sativa* (green wave) (about 1 g) was cut into 0.5-cm square pieces using a surgical knife, to thereby prepare leaf discs. The leaf discs were immersed in 500 mM mannitol, and shaken for 1 hour. The leaf discs were immersed in 50 ml of a protoplastization enzyme solution (1.0% cellulose RS (Yakult Honsha Co., Ltd.), 0.25% macerozyme R-10 (Yakult Honsha Co., Ltd.), 400 mM mannitol, 8 mM $CaCl_2$, and 5 mM Mes-KOH, pH 5.6) and shaken at room temperature for 2 hours. The protoplast suspension was passed through meshes of 100 μm and 40 μm to remove the leaf discs. The protoplast suspension was centrifuged at 60 g for 5 minutes to precipitate the protoplast. The protoplast was resuspended in an aqueous solution containing 167 mM mannitol and 133 mM $CaCl_2$, and the suspension was centrifuged at 40 g for 5 minutes. The protoplast was resuspended in an aqueous solution containing 333 mM mannitol and 66.7 mM $CaCl_2$, and the suspension was centrifuged at 40 g for 5 minutes. The protoplast was suspended in W5 solution (154 mM NaCl, 125 mM $CaCl_2$, 5 mM KCl, 2 mM Mes-KOH, pH 5.6), and the suspension was allowed to stand on ice for 1 hour. The protoplast suspension was centrifuged at 40 g for 5 minutes, and the protoplast was suspended in MaMg solution (400 mM mannitol, 15 mM $MgCl_2$, and 4 mM Mes-KOH, pH 5.6) to a protoplast concentration of $2\times10^6$ cells/ml.

The GFP reporter expression vector, Stx2eB expression vector, modified Stx2eB expression vector, and Stx2eA expression vector prepared above were each separately mixed with 120 μl of a protoplast suspension, and 140 μl of a PEG solution (400 mM mannitol, 100 mM $Ca(NO_3)_2$, and 40% PEG) was added and gently blended, followed by incubation for 7 minutes. Then, 1 ml of W5 solution was added to the protoplast suspensions over about 20 minutes. To the protoplasts precipitated by centrifugation was added 1 ml of a solution obtained by mixing 400 mM mannitol with W5 solution at a ratio of 4:1. LS medium containing 1% sucrose, 400 mM mannitol, and 0.3 mM carbenicillin was added in an amount of 1 ml to the protoplasts precipitated by centrifugation, and culture was performed in the dark at 25° C. for 24 hours.

(6) Western Analysis

To the protoplasts precipitated by centrifugation was added 30 μl of SDS-sample buffer (4% (w/v) SDS, 20% (w/v) glycerol, 0.05% (w/v) bromophenol blue, 300 mM (3-mercaptoethanol, 125 mM Tris-HCl, pH 6.8), followed by thermal denaturation at 95° C. for 2 minutes, to thereby prepare samples. Proteins were separated in a 15% acrylamide gel and blotted on a PVDF membrane (Hybond-P; Amersham) using an electro transfer system. An anti-HA antibody (No. 11 867 423 001, Roche) was used to detect Stx2eB and Stx2eA.

The results are shown below.

(a) Expression of GFP Expression Vector

Figure 8:
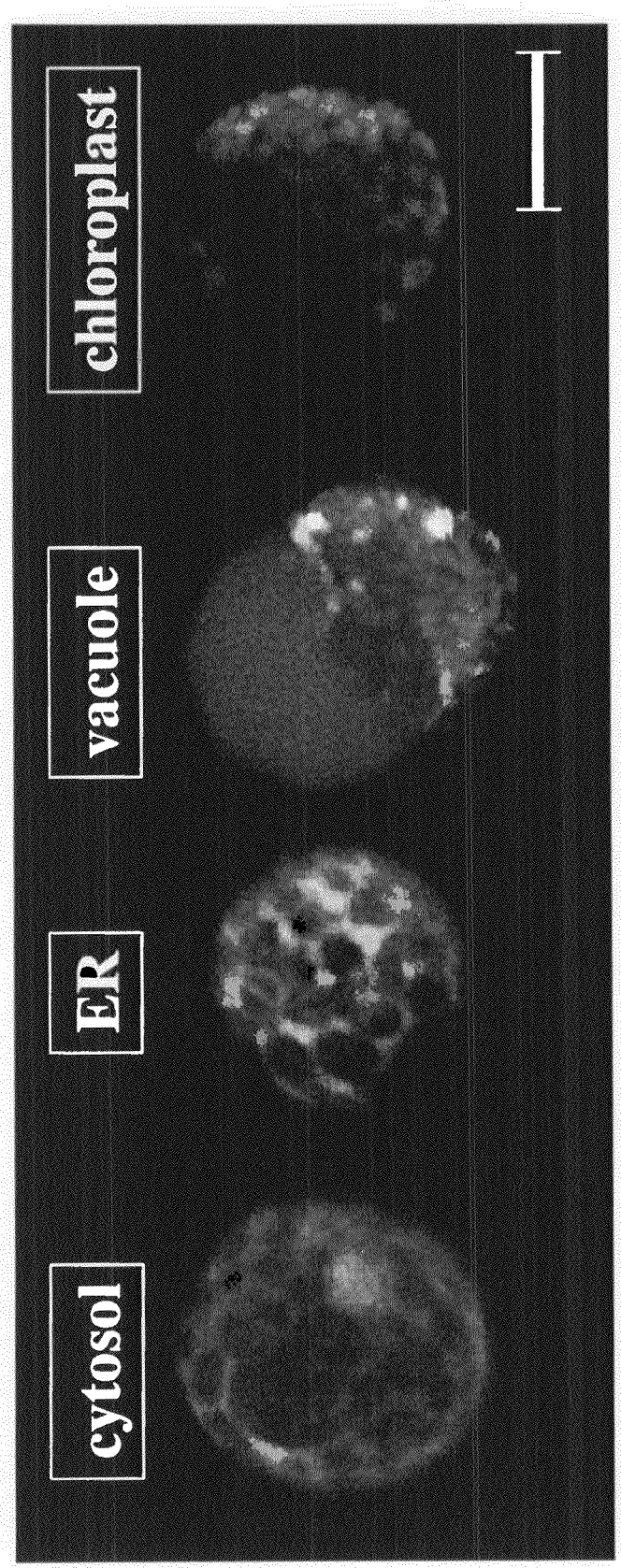
FIG. 8 A diagram showing expression states of GFP reporters in protoplast of *Lactuca sativa* (pictures).

The GFP expression vectors prepared in the section (1) were each introduced into the protoplast of *Lactuca sativa* to transiently express a reporter gene. GFP fluorescence observation was performed using a confocal laser microscope to analize the expression levels of the GFP reporter genes (FIG. 8).

In the case of expression of the cytosol-type GFP, fluorescent signals were detected in regions that were considered as cytosol around chloroplasts and in nuclears. Note that it has been reported that a low-molecular-weight protein such as GFP can pass through a nuclear membrane pore even if it has no nuclear transport signal peptide.

Subsequently, a transport signal to a vesicular transport route was examined. In the case where any of apoplast-type, endoplasmic reticulum-type, and vacuole-type GFP's was expressed, fluorescence was detected in regions that were considered as endoplasmic reticulums during the early protoplast culture period. As the time for culturing the protoplast passed, in the case of the apoplast-type GFP, fluorescent signals disappeared (conceivably, the protein was secreted outside the cell), while in the case of vacuole-type GFP, signals were detected in a large vacuole accounting for the large portion of the cell volume. On the other hand, in the case of the endoplasmic reticulum-type GFP, fluorescence remained in the endoplasmic reticulum.

Meanwhile, a chloroplast transport signal peptide was examined. In the case where the chloroplast-type GFP was expressed, green signals were detected in the chloroplast regions, which emitted red autogenous fluorescence.

Those results reveal that addition of a signal peptide can control localization of a recombinant protein in cells of *Lactuca sativa*.

Figure 9:
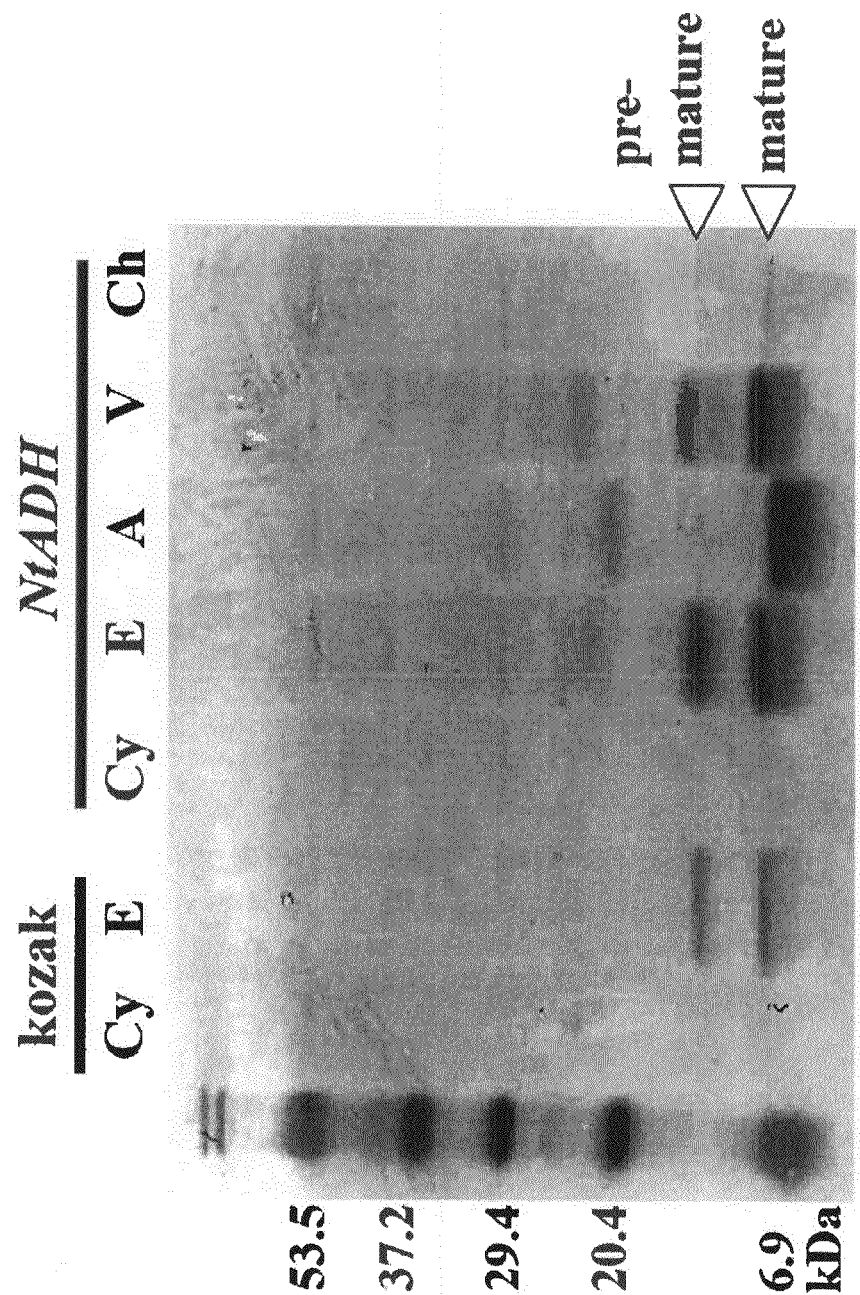
FIG. 9 A diagram showing amounts of Stx2eB accumulated in protoplast of *Lactuca sativa* transformed with expression vectors of Stx2eB added with each of signal peptide (picture).

(b) Effects of Localization Signals and Translational Enhancer in Production of Stx2eB The Stx2eB expression vectors prepared in the section (2) were each introduced into the protoplast of *Lactuca sativa* to transiently express Stx2eB, and Western analysis using an anti-HA antibody was performed to evaluate amounts of accumulated Stx2eB. The results are shown in FIG. 9.

In the case where cytosol-type Stx2eB was expressed using a Kozak sequence, Stx2eB was not detected at all, while in the case where endoplasmic reticulum-type Stx2eB was expressed, Stx2eB precursor (about 12 kDa, pre-mature) including S.P. and Stx2eB (about 8 kDa, mature) were detected.

In the case where cytosol-type Stx2eB was expressed using NtADH 5'UTR, the Stx2eB was not detected, while in the cases where endoplasmic reticulum-type Stx2eB and vacuole-type Stx2eB were expressed, the Stx2eB precursor including S.P. and the Stx2eB were detected. In addition, in the case where apoplast-type Stx2eB was expressed, the Stx2eB was detected. Moreover, in the case where chloroplast-type Stx2eB was expressed, Stx2eB was detected.

Observation of bands in the lanes of Kozak-ER (endoplasmic reticulum-type) and NtADH-ER (endoplasmic reticulum-type) verified that Stx2eB expression levels in the cases of using NtADH 5'UTR were significantly higher than those in the cases of using the Kozak sequence.

In addition, it was found that the amounts of accumulated Stx2eB in plant cells could be increased by feeding the Stx2eB to a vesicular transport route. There were small differences in the amounts of accumulated Stx2eB in the different three sections (endoplasmic reticulum, apoplast, and vacuole) in the vesicular transport route.

(c) Effect of Stx2eB Codon Modification on Expression

Figure 10:
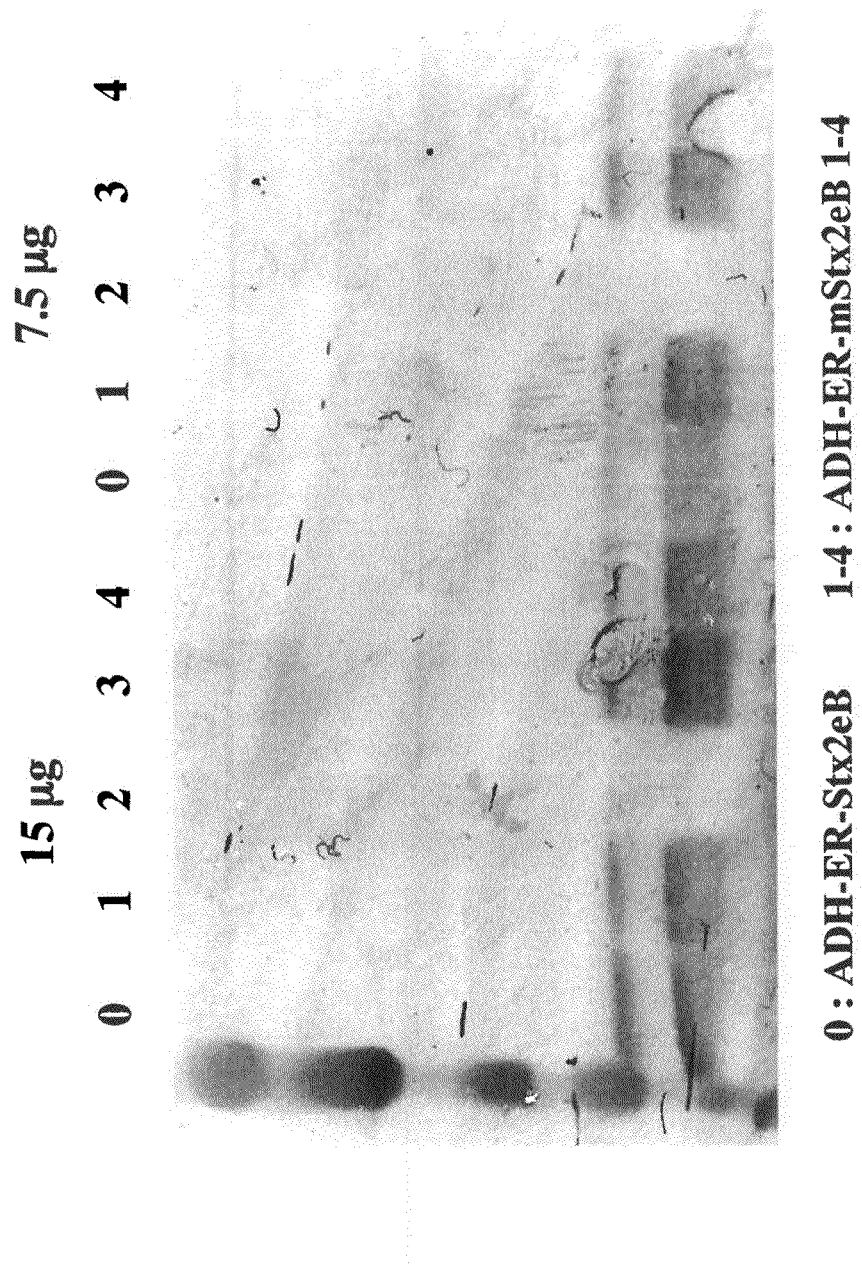
FIG. 10 A diagram showing amounts of Stx2eB accumulated in protoplast of *Lactuca sativa* transformed with expression vectors of codon-modified Stx2eB added with of endoplasmic reticulum retention signal peptides (picture).
Figure 11:
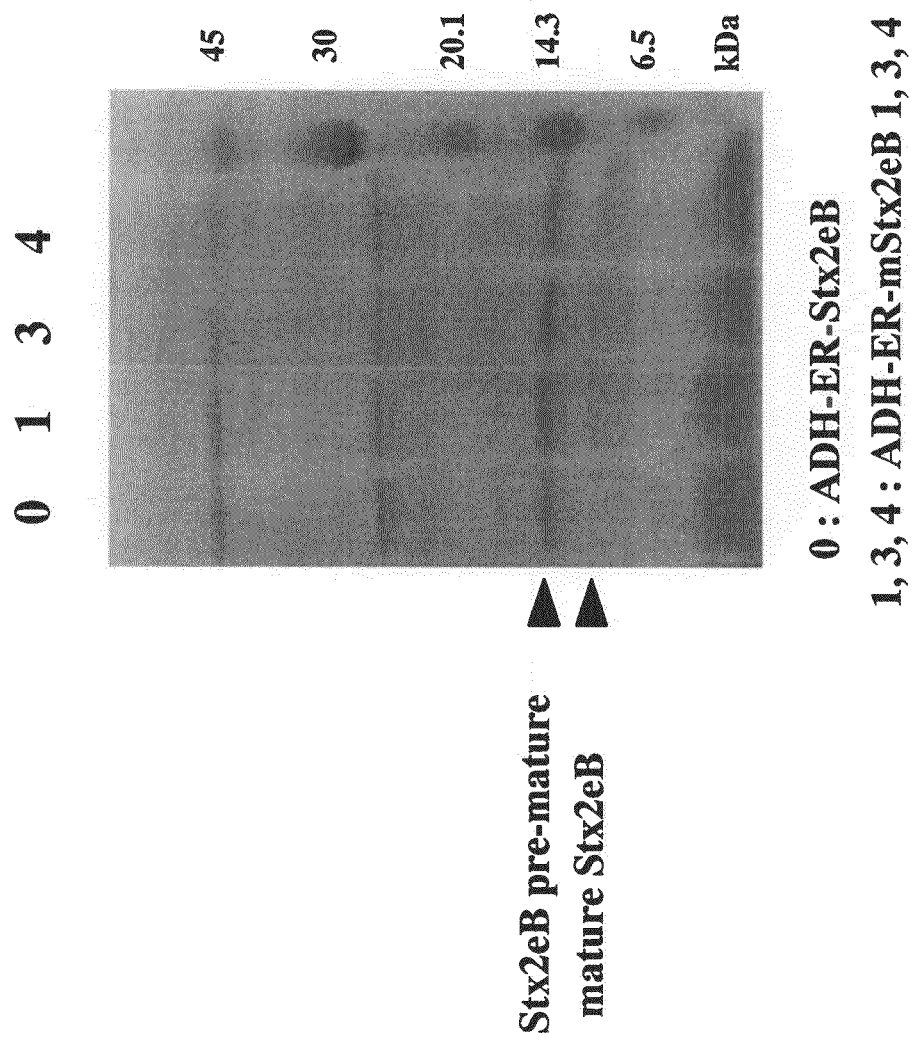
FIG. 11 A diagram showing amounts of Stx2eB accumulated in protoplast of *Lactuca sativa* transformed with expression vectors of codon-modified Stx2eB added with endoplasmic reticulum retention signal peptides (picture).

The codon-modified Stx2eB expression vectors were each introduced into the protoplast of *Lactuca sativa* to transiently express a codon-modified Stx2eB, and Western analysis using an anti-HA antibody was performed to evaluate amounts of accumulated Stx2eB. The results are shown in FIGS. 10 and 11.

In all the lanes: lane 0 (ADH-ER-Stx2eB), lane 1 (ADH-ER-mStx2eB1), lane 2 (ADH-ER-mStx2eB2), lane 3 (ADH-ER-mStx2eB3), and lane 4 (ADH-ER-mStx2eB4), Stx2eB precursor (about 12 kDa, pre-mature) including S.P. and Stx2eB (about 8 kDa, mature) were detected, but in lane 2, the proteins were detected in small amounts.

The results reveal that, in the cases of using ADH-ER-mStx2eB1, ADH-ER-mStx2eB3, and ADH-ER-mStx2eB4 having the base sequences of SEQ ID NOS: 75, 77, and 78, respectively, the amounts of the accumulated Stx2eB protein are particularly high.

(2) Effect of Translational Enhancer in Production of Stx2eA

Figure 12:
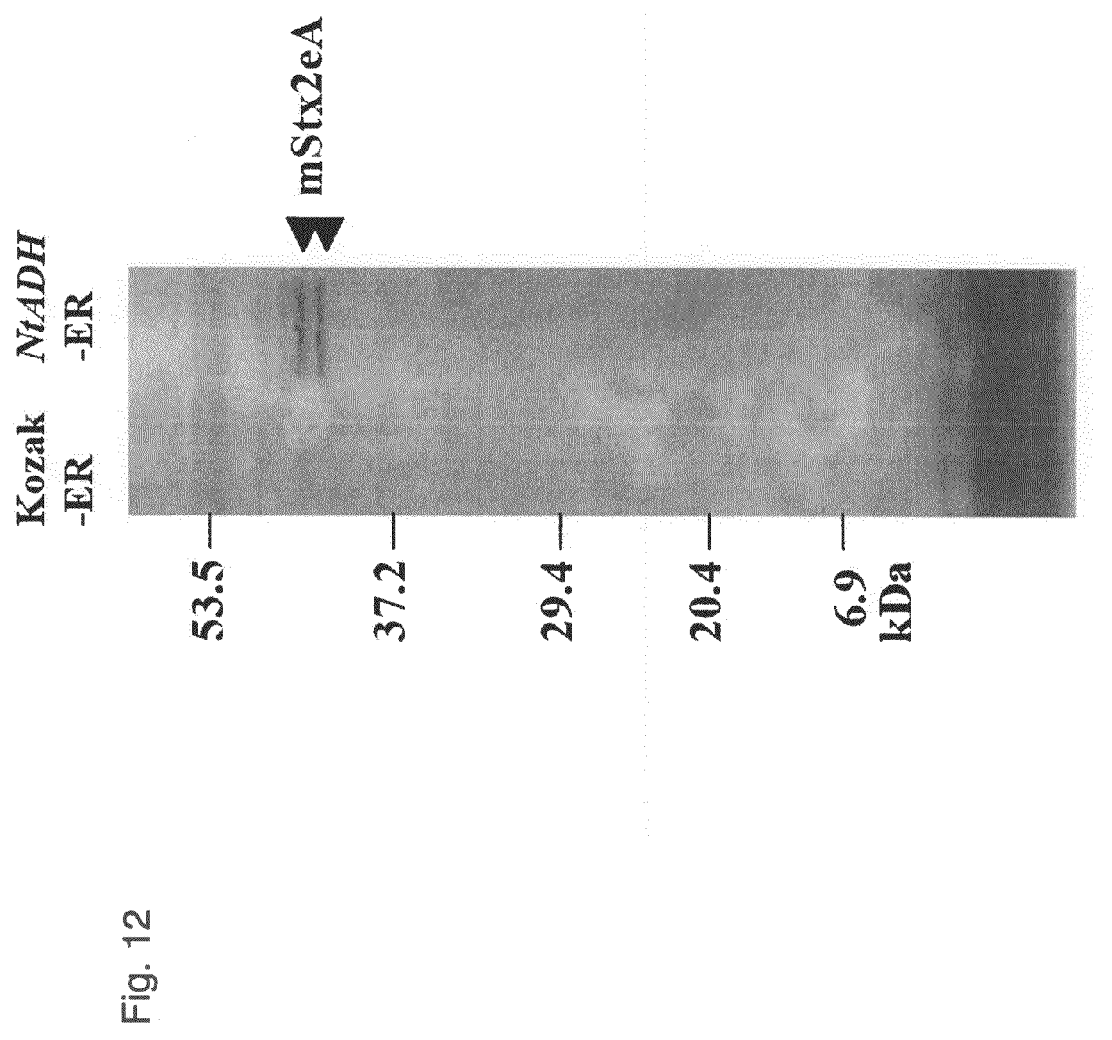

The Stx2eA expression vectors were each introduced into the protoplast of *Lactuca sativa* to transiently express Stx2eA, and Western analysis using an anti-HA antibody was performed to evaluate amounts of accumulated Stx2eA. The results are shown in FIG. 12.

In the case where NtADH-ER-Stx2eA (endoplasmic reticulum-type) was expressed, two bands were detected at the positions of about 34 kDa and about 38 kDa. On the other hand, in the case where Kozak-ER-Stx2eA was expressed, the Stx2eA expression level was the detection limit or less.

The results reveal that Stx2eA expression level in the case of using NtADH 5'UTR was significantly higher than that in the case of using the Kozak sequence.

(8) Determination of Stx2eB Effective Production Amount and Performance Evaluation (a) Purification of Stx2eB-GST Fused Protein In order to produce a fused protein of Stx2e B-subunit and glutathione S-transferase (GST), Stx2eB was subcloned so that a frame was adjusted on the GST3'-side of an *Escherichia coli* protein expression vector, pGEX-6P-1, followed by transformation of *Escherichia coli*. Isopropyl β-D-1-thiogalactopyranoside (IPTG) was added by a conventional method to induce expression of a recombinant (r) Stx2eB-GST fused protein, and purification was performed using a Glutathione Sepharose 4B column by the following method.

Figure 13:
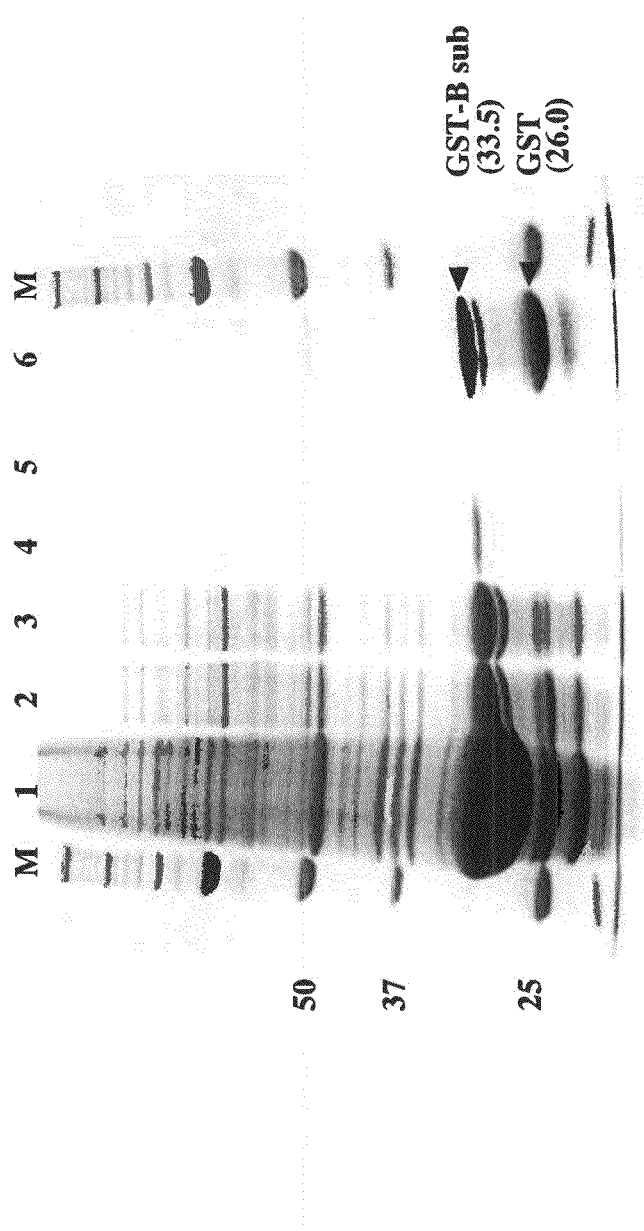
FIG. 13 A diagram showing the results of SDS-PAGE analysis for Stx2eB-GST fused protein (picture). M: marker, 1:Stx2eB 8M urea solution, 2: refolded Stx2eB-GST solution (applied sample), 3: unbound fraction, 4: fraction eluted by the first washing, 5: fraction eluted by the second washing, 6: eluted sample (bound fraction).

The Stx2eB-GST fused protein was expressed in *Escherichia coli*, and the cells were suspended in an aqueous buffer and subjected to sonication. As a result, the supernatant was found to contain the fused protein in a small amount, and therefore the fused protein was found to be present in the insoluble fraction. Then, the fused protein was solubilized with 8 M urea and purified using the column, followed by refolding (FIG. 13).

(b) Experiment of Nasal Administration of Protein to Mouse (Determination of Antibody Titer)

Figure 14:
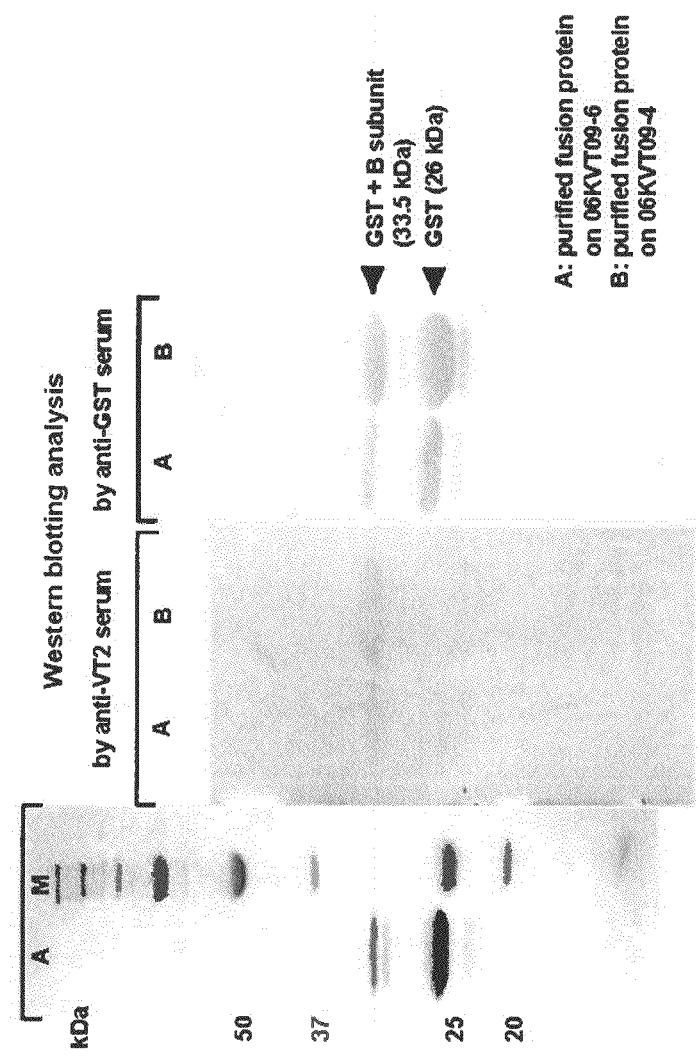
FIG. 14 A diagram showing the results of Western blotting using an anti-VT2 antibody (picture).

For the eluted Stx2eB-GST fused protein, Western blotting was performed using an antibody against Stx2e (anti-VT2 antibody). As a result, two specific bands corresponding to the molecular weights of the Stx2eB-GST fused protein and Stx2eB were detected, and the fused protein was confirmed to retain the antigenicity (FIG. 14).

Figure 15:
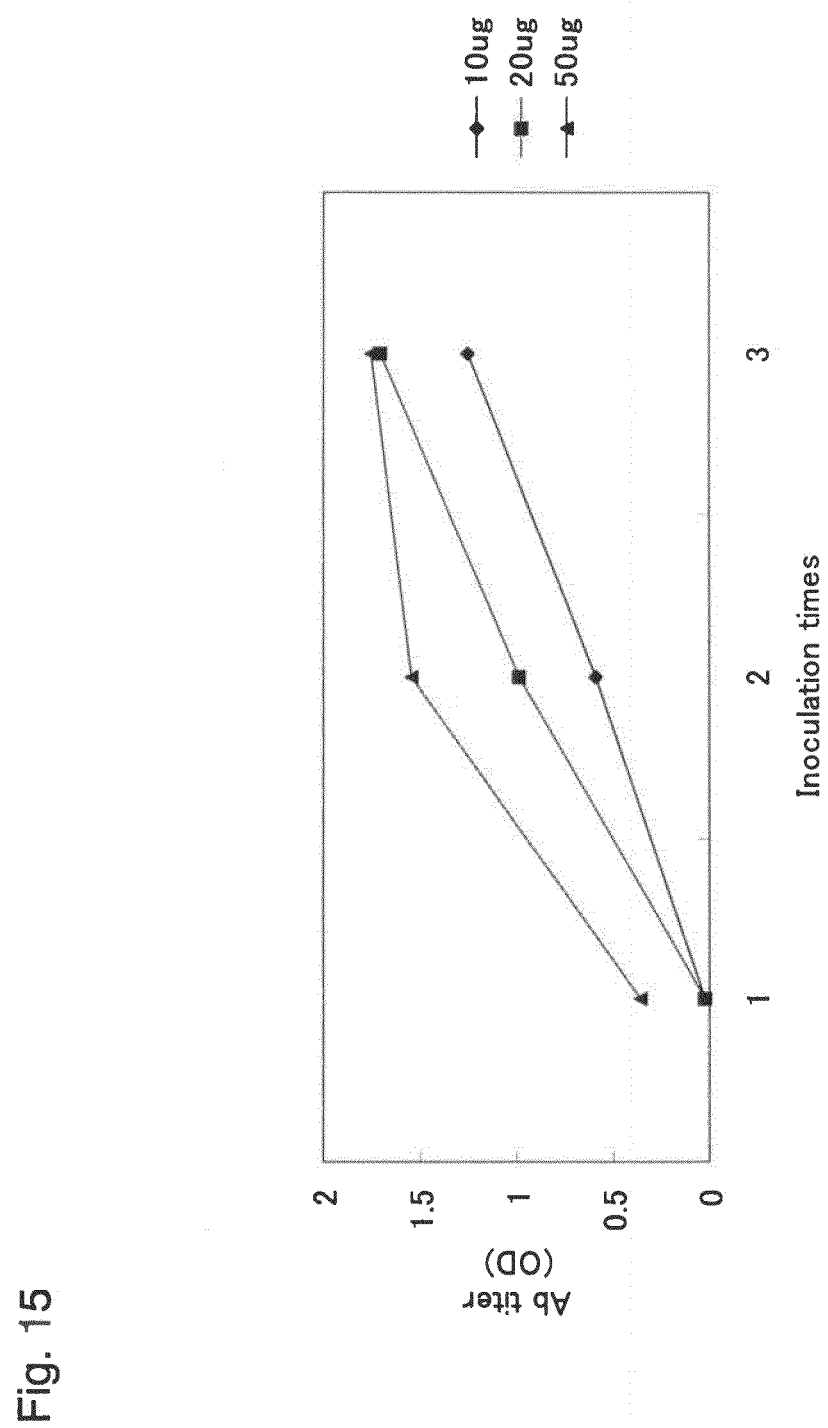
FIG. 15 A diagram showing results of antibody titer determination by nasal administration of Stx2eB-GST fused protein.

Subsequently, the purified Stx2eB-GST fused protein (10, 20, and 50 µg) was nasally administered to mice three times at intervals of one week. On weeks 0, 1, 2, and 3, blood was sampled, and ELISA was performed using the fused protein as an antigen to determine IgG antibody titers. As a result, the antibody titer for the group administered with 50 µg of the fused protein was raised on week 1 of the administration, and on week 2 of the administration, the antibody titers for the groups administered with 10 and 20 µg of the fused protein were raised and increased with time until the third week (FIG. 15).

(9) Production of Stx2eB (a) Construction of Stx2eB Expression Binary Vector In order to produce an Stx2eB using a stable transformant of a plant, ADH-ER-Stx2eB was subcloned in a transformation vector. That is, ADH-ER-Stx2eB was inserted into pBI121 (Clontech) using XbaI and SacI, and the resultant product was arranged between a cauliflower mosaic virus 35S RNA promoter (35S pro.) and a nopaline synthase gene transcription terminator (NOS-T), to thereby prepare an Stx2eB expression binary vector.

(b) Preparation of *Agrobacterium* Transformant

A single colony of *Agrobacterium tumefacience* EHA105 (Hood E E, Gelvin S B, Melchers L S, Hoekema A (1993) New *Agrobacterium* helper plasmids for gene transfer to plants. Transgenic Res. 2: 208-218) was inoculated into 5 ml of YEB medium (Bacto-peptone 5 g/l, Beaf extract 5 g/l, Yeast extract 1 g/l, sucrose 5 g/l, $MgSO_4 \cdot 7H_2O$ 0.5 g/l) and cultured with shaking at 28° C. overnight. The culture solution was inoculated into 500 ml of YEP medium and cultured at 28° C. until the turbidity at 600 nm reached 0.5. The culture solution was centrifuged (5,000 rpm, 10 minutes, 4° C.; BECKMAN JLA-10,500 rotor) to collect the cells, and the supernatant was discarded. The cells were suspended in 500 ml of sterilized water to wash the cells, and the suspension was centrifuged (5,000 rpm, 10 minutes, 4° C.; BECKMAN JLA-10,500 rotor) again to collect the cells, followed by discarding of the supernatant. The procedure was repeated twice, and the precipitates were suspended in 20 ml of cooled sterilized 10% glycerol. The suspension was added to a NALGENE tube and centrifuged (5000 rpm, 10 min, 4° C. BECKMAN JLA-10, 500 rotor) to collect the cells, and the supernatant was discarded. The precipitates were suspended in 3 ml of cooled sterilized 10% glycerol, and the suspension was dispensed in 40 µl aliquots in 1.5-ml microcentrifuge tubes. The tubes were frozen in liquid nitrogen and stored at −80° C.

Competent cells were thawed in ice, and 1 to 2 µl of the binary vector solution was added thereto, and the whole was added to an ice-cooled 2-mm cuvette. An electric pulse (2.5 KV, 25 µF, 400Ω) was applied using an electroporator (BIO RAD, Gene Pulser) to introduce the vector. 1 ml of SOC medium was added, and shaking culture was performed at 28° C. for 1 hour. Then, spindown was performed to remove almost all the supernatant and to collect the cells, and the cells were suspended in the residual medium and spread on LB agar medium containing a suitable antibiotic, followed by culture at 30° C. for two nights.

(c) Preparation of *Nicotiana tabacum* Transformant

Transformation of *Nicotiana tabacum* BY2 culture cells was performed in accordance with the method of An (An G (1985) High efficiency transformation of cultured tobacco cells. Plant Physiol. 79: 568-570). 100 μl of an *Agrobacterium* culture solution obtained by culturing the *Agrobacterium* transformant cells prepared in accordance with the method in the section (b) above in 5 ml of LB medium containing 100 mg/l kanamycin at 28° C. for two nights and 5 to 10 ml of *Nicotiana tabacum* BY2 culture cell suspension on day 4 of culture were added to a petri dish and mixed well, and the dish was allowed to stand at 25° C. for two nights in the dark to perform coexistence culture. In order to remove *Agrobacterium*, the culture solution in the dish was transferred to a 15-ml centrifuge tube and centrifuged (1000 rpm, 5 minutes, 4° C.; BECKMAN GS-6KR centrifuge), and the supernatant was removed. A fresh modified LS medium was added, and centrifugation (1000 rpm, 5 minutes, 4° C.; BECKMAN GS-6KR centrifuge) was performed to wash the cells. The procedure was repeated four times to remove *Agrobacterium*, and *Nicotiana tabacum* BY2 culture cells were spread on a modified LS agar medium containing 100 mg/l kanamycin, followed by static culture in the dark at 25° C. About two or three weeks later, callus cells were transplanted to a new plate, and proliferated clones were selected. The clones were transferred to 30 ml of modified LS medium containing 100 mg/l kanamycin and subcultured.

(d) Western Analysis

Figure 16:
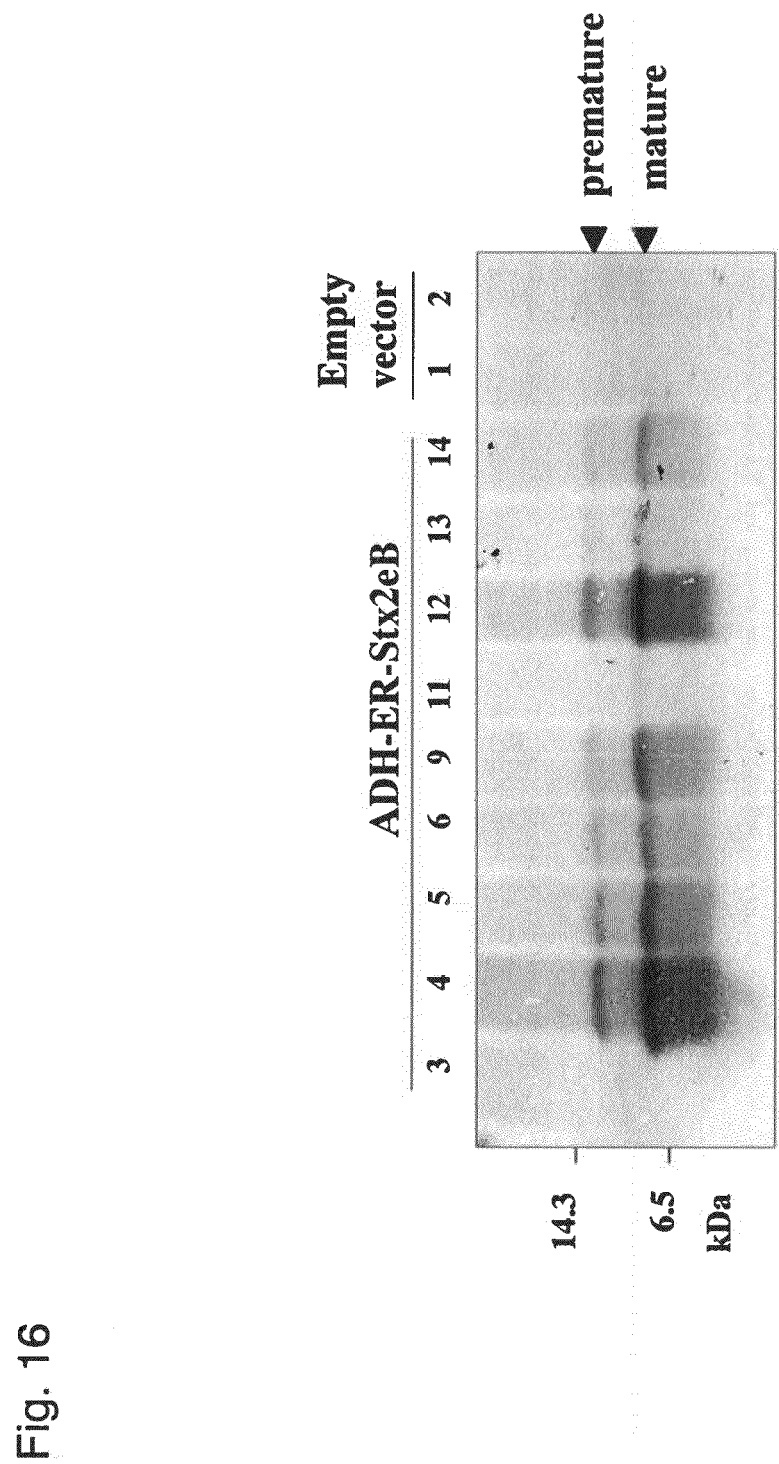
FIG. 16 A diagram showing amounts of Stx2eB accumulated in *Nicotiana tabacum* BY2 cultured cells transformed with an expression vector of Stx2eB added with endoplasmic reticulum retention signal peptides (picture).

The amounts of accumulated Stx2eB in the *Nicotiana tabacum* transformant BY2 culture cells prepared above were evaluated by Western analysis using the anti-HA antibody in the same way as above. The results are shown in FIG. 16. In FIG. 16, the numbers of the respective lanes represent independent strains. The "Empty vector" is a vector obtained by introducing only a vector pBI121 containing no "ADH-ER-Stx2eB".

(10) Production of Stx2eB (a) Design of Codon-Modified Stx2eB

A sequence including selected codons that have high GC contents and are less frequently used in *Lactuca sativa* was designed as a codon-modified Stx2eB. The prepared codon-modified Stx2eB was designated as mStx2eB5 (SEQ ID NO: 79).

The designed base sequences of mStx2eB5 were compared by CLUSTALW (http://align.genome.jp/) (FIG. 17). The ratio of the sequence XXG/C(X: any base) of Stx2eB before and after codon modification was 100%, and the GC ratio was 62.4%.

(b) Preparation of Codon-Modified Stx2eB

Based on the designed base sequences of mStx2eB5, primers having six base sequences were prepared. Those primers were used to prepare mStx2eB5 by using those primers in the same way as the method of producing codon-modified Stx2eB described in the section (3) above.
Primers
A: SEQ ID NO: 80
B: SEQ ID NO: 81
C: SEQ ID NO: 82
D: SEQ ID NO: 83
E: SEQ ID NO: 84
F: SEQ ID NO: 85

(c) Construction of Codon-Modified Stx2eB Expression Binary Vector

In order to produce a codon-modified Stx2eB using a stable transformant of a plant, ADH-ER-mStx2eB 1-5 (SEQ ID NOS: 75 to 78, and 86) were subcloned in a transformation vector using mStx2eB 1-4 prepared in the section (3) above and mStx2eB5 prepared in the section (b). That is, ADH-ER-mStx2eB 1-5 were separately inserted into pBI121 (Clontech) using XbaI and SacI, and the resultant products were arranged between a cauliflower mosaic virus 35S RNA promoter (35S pro.) and a nopaline synthase gene transcription terminator (NOS-T), to thereby prepare mStx2eB 1-5 expression binary vectors.

(d) Preparation of *Agrobacterium* Transformant

The mStx2eB 1-5 expression binary vectors prepared in the section (c) were introduced into *Agrobacterium* tumefacience EHA105 in the same way as the method described in the section (9)(b) above, to thereby yield *Agrobacterium* transformants.

(e) Preparation of *Nicotiana tabacum* Transformant

The mStx2eB 1-5 expression binary vectors were separately introduced into *Nicotiana tabacum* BY2 culture cells in the same way as the method described in the section (9)(c) above using the cells of the *Agrobacterium* transformants obtained in the section (b), to thereby yield *Nicotiana tabacum* transformants.

In addition, transient expression test using *Lactuca sativa* protoplast was performed in the same way as above.

(f) Western Analysis

Figure 18:
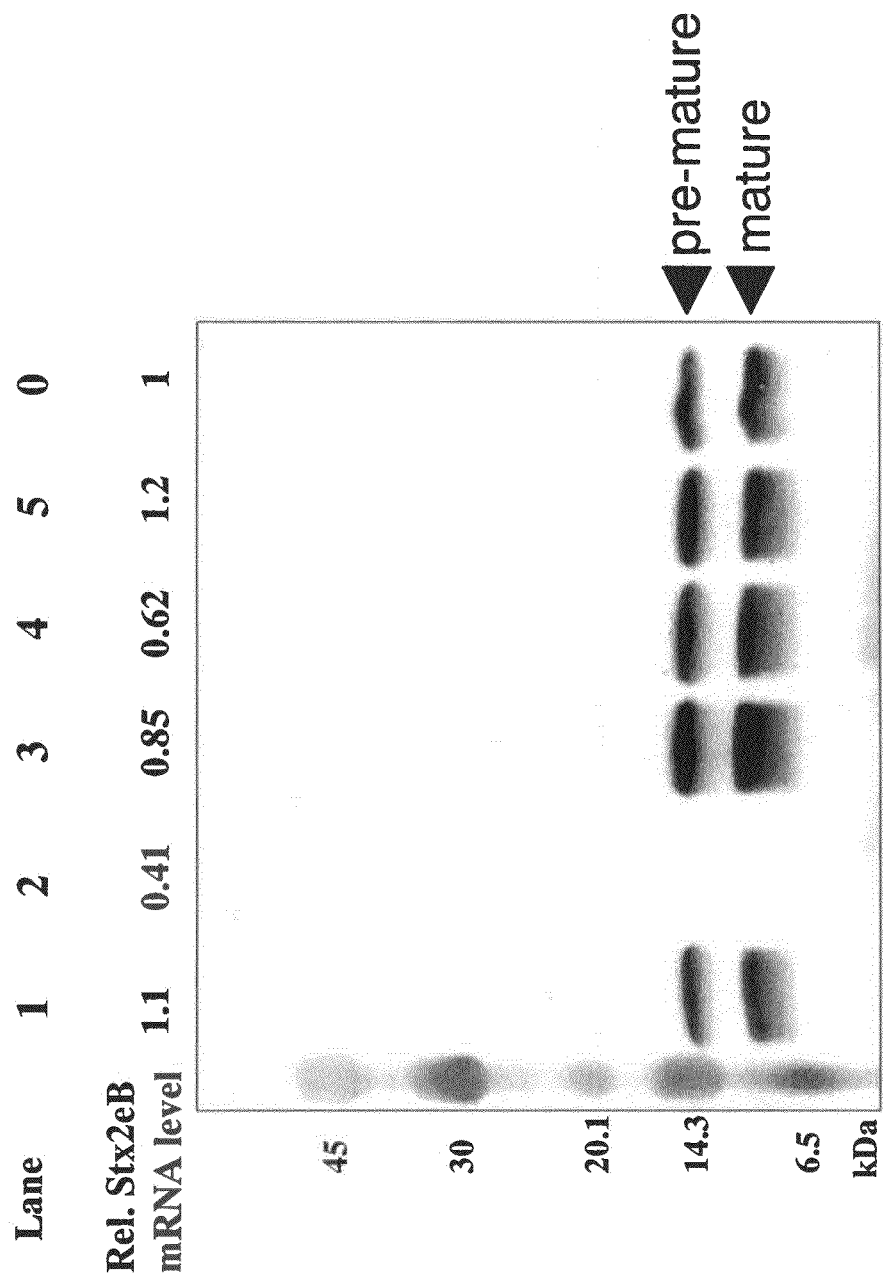
FIG. 18 A diagram showing amounts of Stx2eB accumulated in *Nicotiana tabacum* BY2 cultured cells transformed with an expression vector of codon-modified Stx2eB added with endoplasmic reticulum retention signal peptides (picture).

The amounts of accumulated Stx2eB proteins in the *Nicotiana tabacum* BY2 culture cells and the *Lactuca sativa* protoplast prepared above were evaluated by Western analysis using the anti-HA antibody in the same way as above. The results are shown in FIG. 18 (*Lactuca sativa* protoplast) and 19 (*Nicotiana tabacum* BY2 culture cells). FIG. 18 also shows the measurement results of the mRNA amounts.

As shown in FIG. 18, in all lanes: lane 0 (ADH-ER-Stx2eB), lane 1 (ADH-ER-mStx2eB1), lane 2 (ADH-ER-mStx2eB2), lane 3 (ADH-ER-mStx2eB3), lane 4 (ADH-ER-mStx2eB4), and lane 5 (ADH-ER-mStx2eB5), Stx2eB precursor (about 12 kDa, pre-mature) including S.P. and Stx2eB (about 8 kDa, mature) were detected, but in lane 2, the proteins were not detected.

Figure 19:
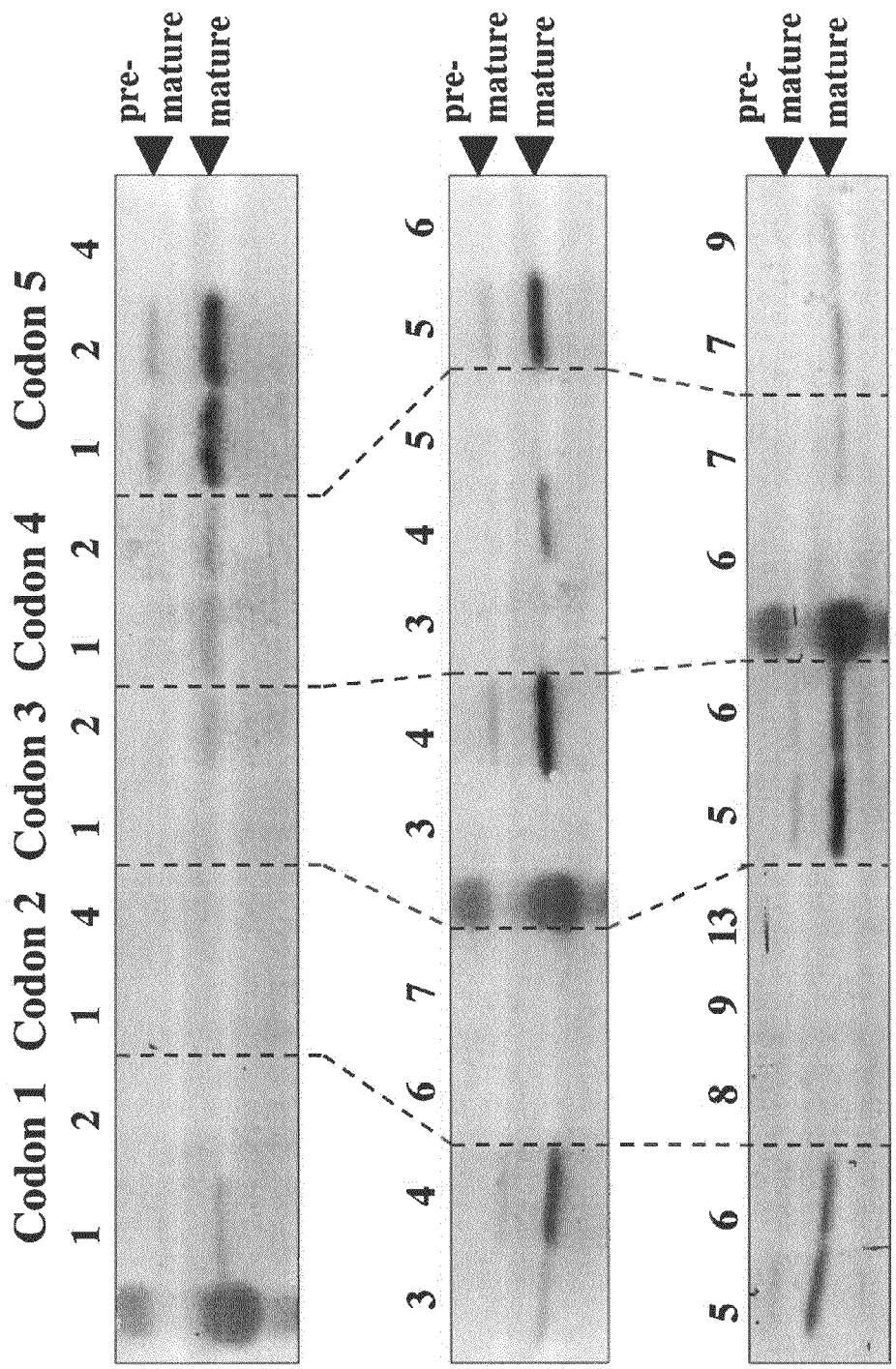
FIG. 19 A diagram showing amounts of Stx2eB accumulated in *Nicotiana tabacum* BY2 cultured cells transformed with an expression vector of codon-modified Stx2eB added with of endoplasmic reticulum retention signal peptides (picture).
Figure 20:
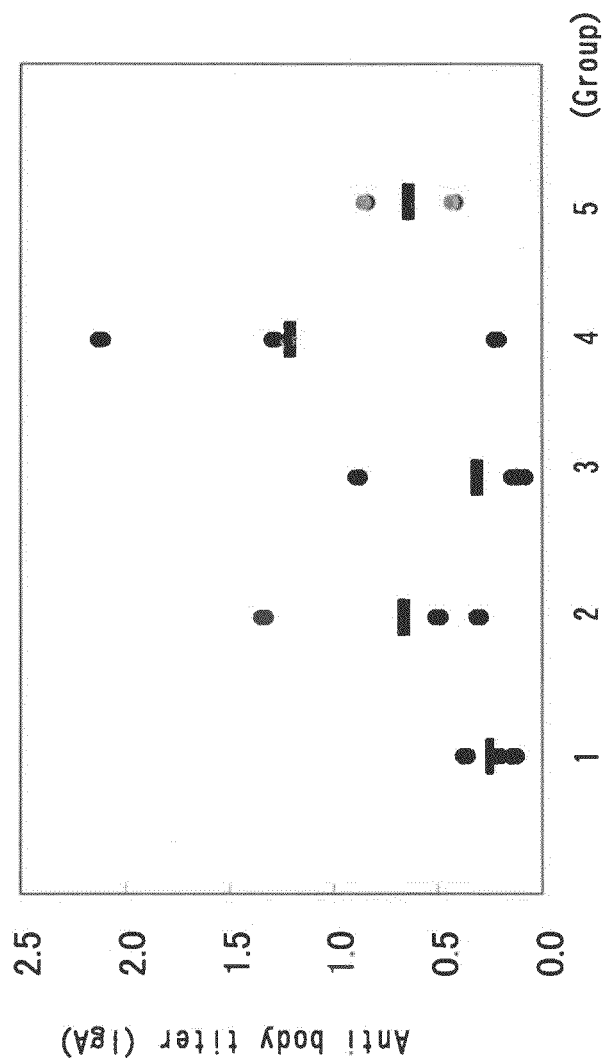
FIG. 20 A diagram showing antibody titers of Stx-specific IgA in stools collected on day 0 of forced administration of an edema disease bacterium.
Figure 21:
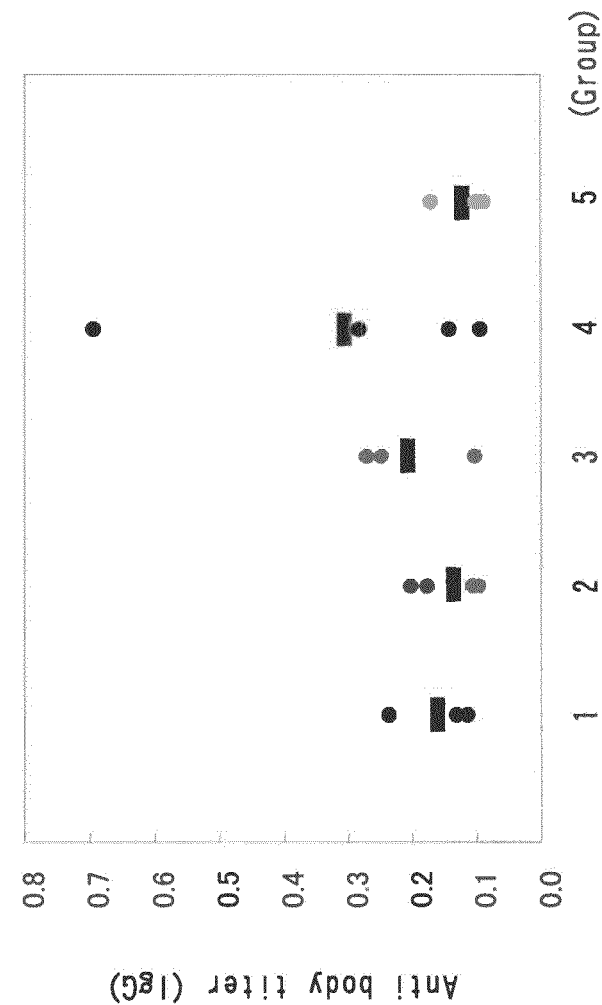
FIG. 21 A diagram showing antibody titers of Stx-specific IgG in blood collected on day 0 of forced administration of an edema disease bacterium.
Figure 22:
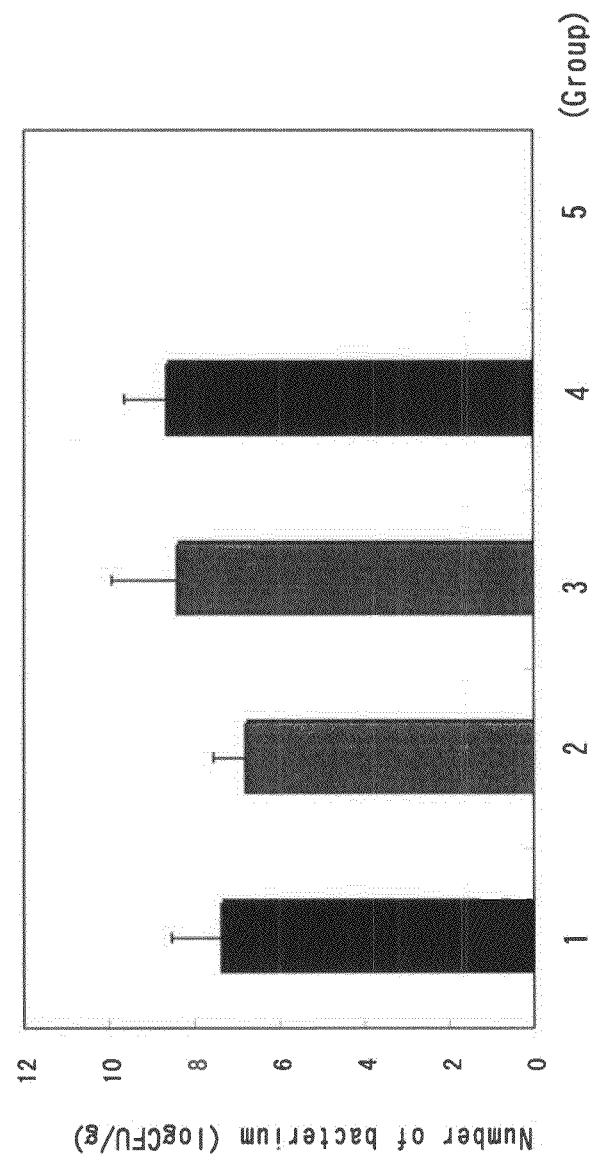
FIG. 22 A diagram showing the number of edema disease bacterium in stools collected on day 3 of forced administration of an edema disease bacterium.
Figure 23:
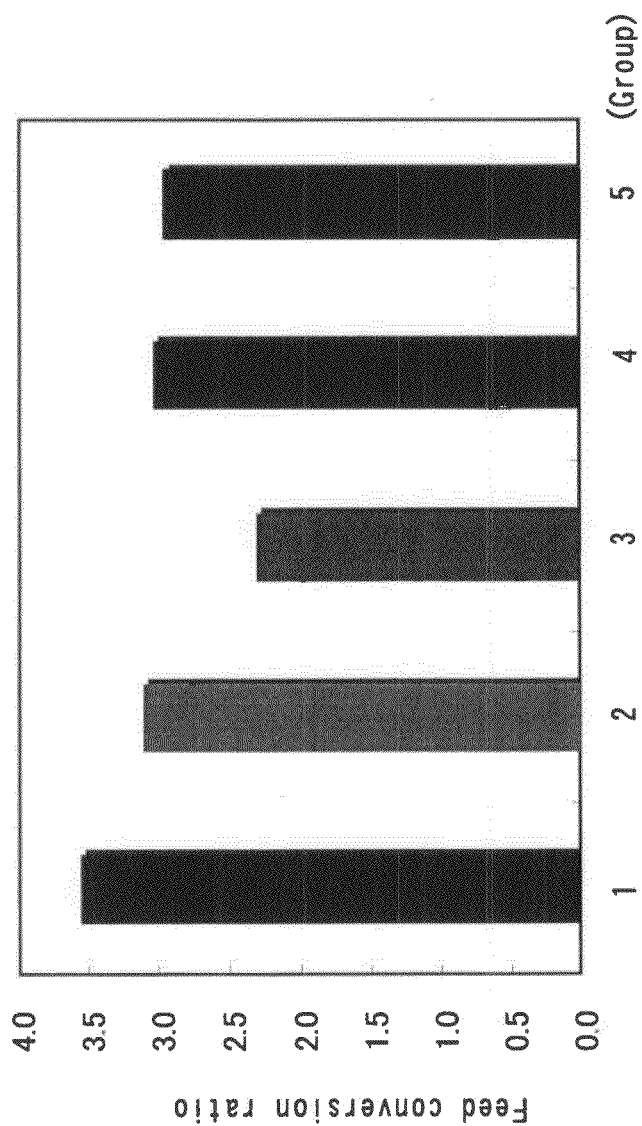
FIG. 23 A diagram showing feed conversion ratios during the entire period.
Figure 24:
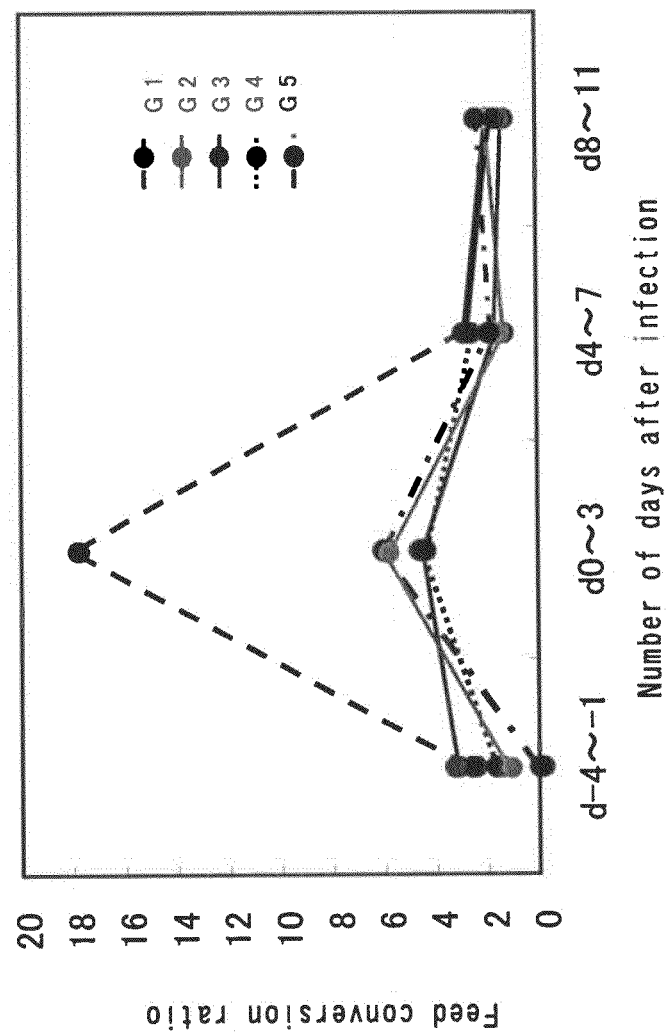
FIG. 24 A diagram showing changes in feed conversion ratios.

In FIG. 19, codons 1 to 5 each represent mStx2eB 1-5. The numbers of the respective lanes represent independent strains. In the cases of mStx2eB1, mStx2eB3, mStx2eB4, and mStx2eB5, proteins were detected for some of the strains, while in the case of mStx2eB2, no protein was detected for all strains. The amounts of proteins detected were compared, and it was found that they were particularly high in the cases of mStx2eB3 and mStx2eB5. That is, the results reveal that design of a codon having a high GC content increased a translation level regardless of the codon usage in *Lactuca sativa*.

(11) Administration Test of Pig Edema Disease Vaccine

(a) Production of Pig Edema Disease Vaccine

The Stx2eB-GST fusion protein purified as described in the section (8)(a) was suspended in PBS at a concentration of 8 mg/ml, to thereby prepare a pig edema disease vaccine.

(b) Preparation of Edema Disease Bacteria Capsule

[Bacterial Strain]

Verotoxin-producing *Escherichia coli* (VTEC) No. 1362-1 isolated from pig clinical sample (derived from a pig that had died at the age of 40 days)

Serover: 0139; fedA, +
Toxin: stx2e, +; ST, +; LT, −

[Preparation]

The above-mentioned strain No. 1362-1 was cultured in TS broth at 37° C. for 4 hours. Bacterial culture was centrifuged, and the precipitate was collected and encapsulated in enteric-coated capsules.

(c) Administration of Vaccine and Edema Disease Bacteria

Among healthy baby pigs in the suckling period raised in a pig farm, 6 baby pigs from each of 3 mother pigs, i.e., a total of 18 baby pigs were selected and divided into 5 groups as shown in Table 4. Each group includes both male and female baby from different mother pigs. At the age of 6, 12, and 18 days, a pig edema disease vaccine was nasally administered to the baby pigs of groups 2 to 4 using a pipette in predetermined doses (per administration) shown in Table 4, and the baby pigs were raised together with the mother pigs at the pig farm until the age of 21 days. On the other hand, 0.5 ml of PBS was nasally administered to the baby pigs of groups 1 and 5. At the age of 21 days, the baby pigs were weaned and divided into each group. They were kept at baby pig barns with concrete floors covered with sawdust where the temperature was controlled by a thermal light. The feed used was SDS No. 1 (manufactured by Nippon Formula Feed Mfg Co. Ltd.), and the pigs were allowed to freely ingest the feed and water. The amounts of the feed ingested and body weights were monitored during the experiment. Four days later, edema disease bacteria-containing capsules were orally inoculated to the baby pigs of groups 1 to 4 once a day for 3 days (25 to 27 days old). To group 5 were forcibly administered enteric-coated capsules containing physiological saline.

TABLE 4

| Test group | Pig edema disease vaccine | Inoculation of edema disease bacteria | Number of pigs |
|---|---|---|---|
| 1 | No administration | Inoculation (for 3 days) | 3 |
| 2 | 1 mg/pig | Inoculation (for 3 days) | 4 |
| 3 | 4 mg/pig | Inoculation (for 3 days) | 4 |
| 4 | 16 mg/pig | Inoculation (for 3 days) | 4 |
| 5 | No administration | No inoculation (administration of physiological saline (for 3 days)) | 3 |

Clinical symptoms were monitored every day during the period from day 0 to day 11 of the oral inoculation of edema disease bacteria. The observation was performed for the following clinical symptoms of edema disease: edema around eyes, neurological symptom, motor function, posture, stool property, appetite, and respiratory status, and clinical symptom scores were recorded based on the following criteria.

Edema around eyes (blepharedema) (0: none, 1: mild, 2: moderate, 3: severe)

Neurological symptom (0: none, 1: mild, 2: moderate, 3: severe)

Motor function (0: normal, 1: decreased, 2: disappeared)

Posture (0: normal, 1: sitting-dog-like, 2: prone•recumbent)

Stool property (0: normal, 1: loose stool, 2: muddy stool, 3: watery stool•mucous and bloody stool)

Appetite (0: normal, 1: slightly poor, 2: poor, 3: lost)

Respiratory status (0: normal, 1: slightly rapid 2: rapid)

Stools were collected on Days 0, 3, 7 and 11, while blood were collected on Days 0 and 11.

(d) Test Results (i) Determination of Antibody Titer

The Stx-specific IgA antibody titers in the stools collected on day 0 were determined by ELISA. The stools were diluted with a 9-fold volume of PBS and suspended, and the suspension was centrifuged to collect the supernatants, which were used as samples for ELISA determination. The results are shown in FIG. 20. Meanwhile, the Stx-specific IgG antibody titers in the blood collected on day 0 were determined by ELISA. The results are shown in FIG. 21. There was no significant difference in the antibody titers between different groups. However, in the groups administered with the edema disease vaccine, some pigs showed high antibody titers.

(ii) Detection of Edema Disease Bacteria

The edema disease bacteria-specific genes in the stools were quantified by PCR, and the numbers of edema disease bacterial cells were calculated. Stool samples collected on Day 3 were used for PCR. DNAs in the stools were extracted using QUICK GENE (FUJIFILM Corporation), and the edema disease bacterial gene was quantified by real-time PCR (in accordance with Tsukahara et al. (2007)), followed by calculation of the numbers of edema disease bacterial cells. The results are shown in FIG. 22. The same number of edema disease bacteria was detected from infected groups (group 1 to 4).

(iii) Calculation of Feed Conversion Rate

From the results of monitoring the dietary intake and body weights, feed conversion rate was determined on 4 to 1 days before the infection (d −4 to −1), and on days 0 to 3 (d 0 to 3), on days 4 to 7 (d 4 to 7), and on days 8 to 11 (d 8 to 11) post infection, respectively. In addition, feed conversion rate during the entire period (d −4 to 11) were calculated. Note that the feed conversion rate refers to an amount of a feed required for increasing 1 kg of body weight during a certain period.

Feed conversion rate=ingested feed amount/increased body weight

FIG. 23 shows feed conversion rate during the entire period, while FIG. 24 shows changes in feed conversion rate. The feed conversion rate during the entire period of group 1 (infected with the edema disease bacteria with no edema disease vaccine) was the highest, while that of group 3 (infected with the edema disease bacteria with administration of 4 mg/pig of the edema disease vaccine) was the lowest. In addition, group 1 showed very high feed conversion rate on days 0 to 3 post infection. An increased feed conversion rate was due to diarrhea which affected the body weight gain in accordance with the amount of the ingested feed.

(iv) Clinical Observation

Figure 25:
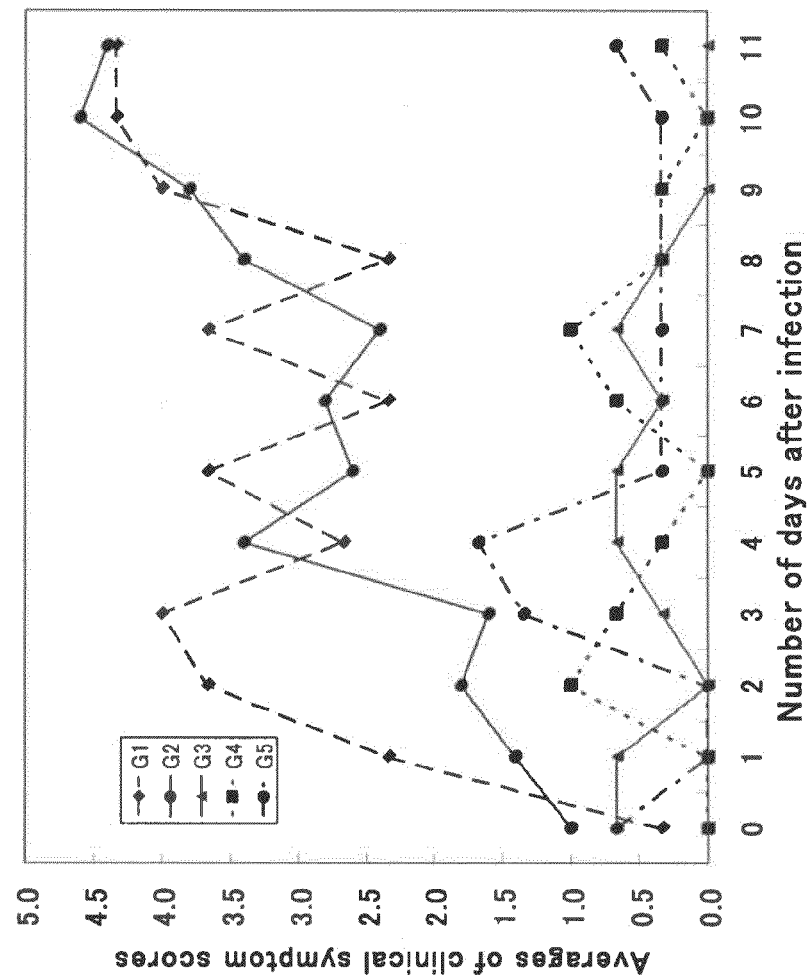
FIG. 25 A diagram showing changes in average clinical symptom scores per baby pig.
Figure 26:
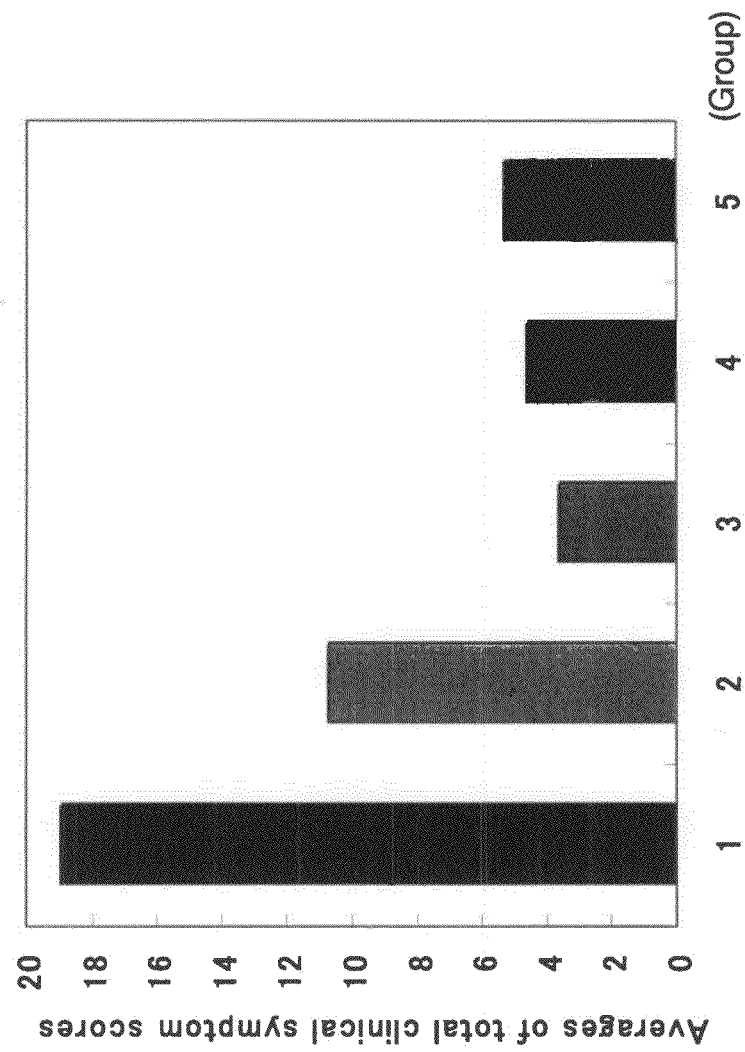
FIG. 26 A diagram showing averages of the total clinical symptom scores per baby pig during the entire period.
Figure 27:
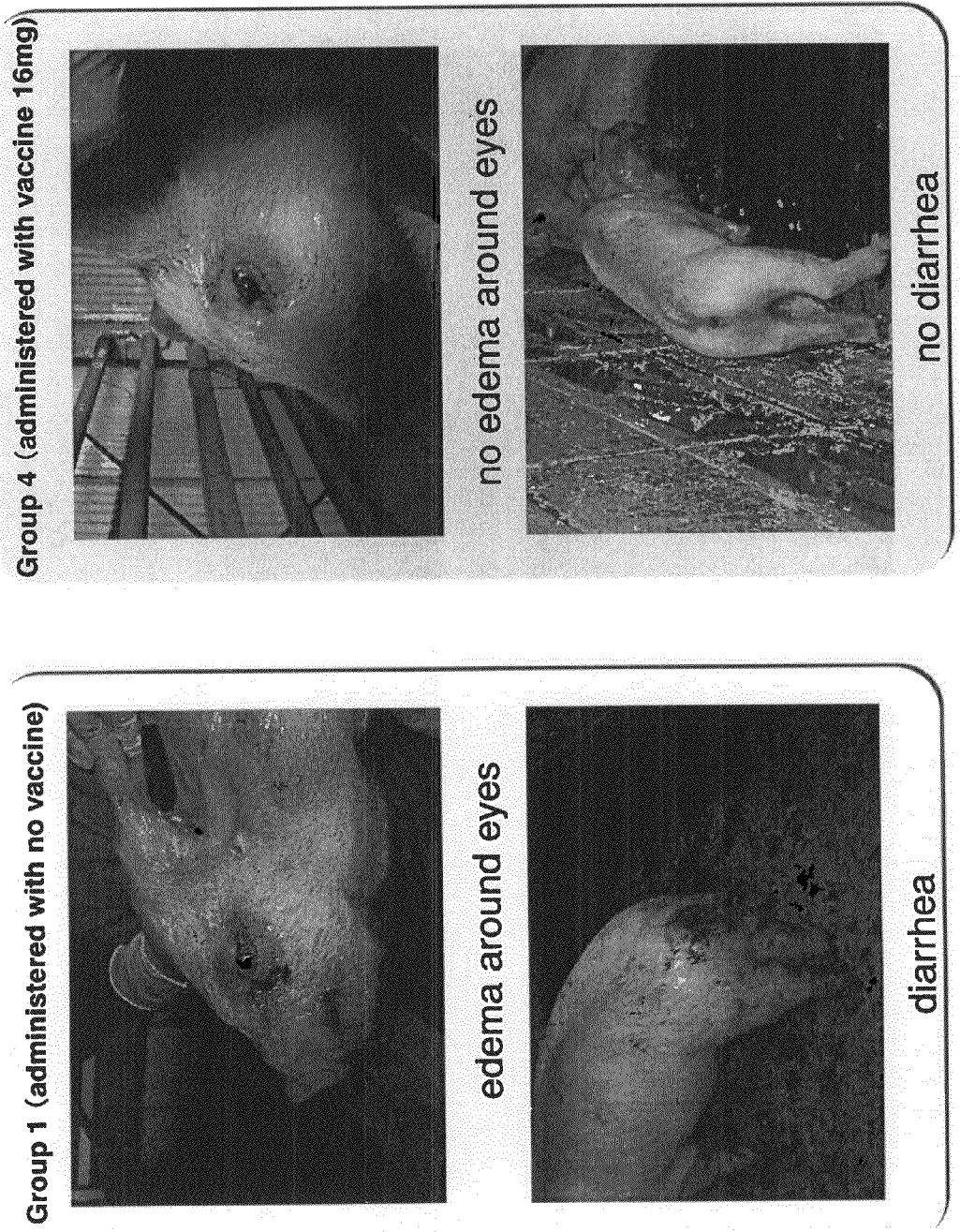
FIG. 27 Pictures of a baby pig of the edema disease vaccine-unadministered group and a baby pig of the edema disease vaccine-administered group on day 11 of administration of an edema disease bacterium.

Based on the clinical symptom scores, average clinical symptom scores for each day were calculated. The changes in average clinical symptom scores are shown in FIG. 25. In addition, the averages of the total clinical symptom scores during the entire period (on 0 to 11 days post infection) per baby pig were calculated. The results are shown in FIG. 26. In group 1, clinical symptoms of edema disease was developed and worsen during 1 to 3 days post infection, the symptoms persisted up to day 11. In group 2 (administered with 1 mg of the edema disease vaccine), clinical symptoms of edema disease was developed, but less severe than group 1. On the other hand, group 3 (administered with 4 mg of the edema disease vaccine) group 4 (administered with 16 mg of the edema disease vaccine), have only mild symptoms, that was comparable to group 5 which was uninfected with the edema disease bacteria. In particular, in the cases of groups 3 and 4, no blepharedema (typical symptom of edema disease) was observed. FIG. 27 shows pictures of representative pigs of group 1 and group 4, respectively. The pig of group 1 administered with no edema disease developed severe edema around the eyes and watery diarrhea. On the other hand, the baby pig of group 4 administered with 16 mg of the edema disease vaccine did not developed edema around the eyes and diarrhea.

Moreover, the total clinical symptom scores during the entire period reveal that administration of the edema disease vaccine can ameliorate or suppress the clinical symptoms of edema disease. In particular, it was found that, the clinical symptoms of edema disease could be effectively suppressed by three-time administration of the edema disease vaccine in an amount of 4 mg or more.

INDUSTRIAL APPLICABILITY

If a plant or the like is transformed with the DNA construct of the present invention, a transformant capable of producing an Stx2e protein can be produced at high efficiency. Use of the DNA construct of the present invention can produce a pig edema disease vaccine at high efficiency using a plant such as Lactuca sativa, which can be cultivated at low cost. In addition, if a pig edema disease vaccine of the present invention is used, the pig edema disease can be easily and efficiently controlled.

The invention claimed is:

1. A *Lactuca sativa* transformed with a recombinant vector comprising a DNA construct, wherein the DNA construct comprises:
   a 5'-untranslated region of an alcohol dehydrogenase gene derived from *Nicotiana tabacum*;
   a DNA encoding a B-subunit of a Stx2e protein, wherein the DNA encoding the B-subunit of a Stx2e protein is operably-linked to the 5'-untranslated region of the alcohol dehydrogenase gene;
   a secretory signal peptide derived from *Nicotiana tabacum* at an amino terminus of the B-subunit of a Stx2e protein; and
   an endoplasmic reticulum retention signal peptide which comprises an HDEL sequence of SEQ ID NO: 14 at a carboxy terminus of the B-subunit of a Stx2e protein,
   wherein the DNA construct does not include an A-subunit of a Stx2e protein.

2. The transformed *Lactuca sativa* of claim 1, wherein the 5'-untranslated region of the alcohol dehydrogenase gene is a DNA having an identity of 90% or more to SEQ ID NO: 1.

3. The transformed *Lactuca sativa* of claim 1, wherein the secretory signal peptide is encoded by a DNA having an identity of 90% or more to SEQ ID NO: 11.

4. The transformed *Lactuca sativa* of claim 1, wherein said DNA construct has a base sequence represented by SEQ ID NO: 12 or hybridizing with a DNA having the base sequences represented by SEQ ID NO: 12 under stringent conditions wherein hybridization is performed in 2×SSC (330 mM NaCl, 30 mM citric acid) and at 42° C.

5. The transformed *Lactuca sativa* of claim 1, wherein said DNA construct has a base sequence represented by SEQ ID NOS: 23, 75, 77, 78, or 86 or hybridizing with a DNA having the base sequences represented by SEQ ID NO: 23, 75, 77, 78, or 86 under stringent conditions wherein hybridization is performed in 2×SSC (330 mM NaCl, 30 mM citric acid) and at 42° C.

6. The transformed *Lactuca sativa* of claim 1, wherein the DNA encoding the B-subunit of a Stx2e protein comprises the amino acid sequence having an identity of 90% or more to SEQ ID NO: 3.

7. The transformed *Lactuca sativa* of claim 1, wherein the DNA encoding the B-subunit of a Stx2e protein encodes a single B-subunit of the subunit of a Stx2e protein.

8. A seed produced by the transformed *Lactuca sativa* of claim 1, wherein the seed comprises the DNA construct.

9. A pig edema disease vaccine, comprising the transformed *Lactuca sativa* of claim 1, wherein the vaccine does not comprise adjuvant.

10. The pig edema disease vaccine of claim 9, which is orally administrable.

11. A method of controlling pig edema disease, comprising administering the pig edema disease vaccine of claim 9 to a pig.

12. A method of producing a B-subunit of a Stx2e protein, comprising expressing the B-subunit of a Stx2e protein in the transformed *Lactuca sativa* of claim 1.

13. A method of inducing an immune response in a pig, comprising administering the pig edema disease vaccine of claim 9 to a pig.

14. A method of inducing an immune response in a pig, comprising administering the pig edema disease vaccine of claim 9 to the pig.

* * * * *

SEQUENCE LISTING

```
<160> NUMBER OF SEQ ID NOS: 86

<210> SEQ ID NO 1
<211> LENGTH: 90
<212> TYPE: DNA
<213> ORGANISM: Nicotiana tabacum

<400> SEQUENCE: 1
atttaactca gtattcagaa acaacaaaag ttcttctcta cataaaattt tcctatttta      60
gtgatcagtg aaggaaatca agaaaaataa                                      90

<210> SEQ ID NO 2
<211> LENGTH: 304
<212> TYPE: PRT
<213> ORGANISM: Escherichia coli

<400> SEQUENCE: 2

Met Lys Cys Ile Leu Leu Lys Trp Ile Leu Cys Leu Leu Leu Gly Phe
1               5                   10                  15

Ser Ser Val Ser Tyr Ser Gln Glu Phe Thr Ile Asp Phe Ser Thr Gln
            20                  25                  30

Gln Ser Tyr Val Ser Ser Leu Asn Ser Ala Ile Ser Thr Pro Leu Glu
        35                  40                  45

His Ile Ser Gln Gly Ala Thr Ser Val Ser Val Ile Asn His Thr Pro
    50                  55                  60

Pro Gly Ser Tyr Ile Ser Val Gly Ile Arg Gly Leu Asp Val Tyr Gln
65                  70                  75                  80

Glu Arg Phe Asp His Leu Arg Leu Ile Ile Glu Arg Asn Asn Leu Tyr
                85                  90                  95

Phe Val Asn Thr Thr Asn Thr Phe Tyr Arg Phe Ser Asp Phe Ala
            100                 105                 110

His Ile Ser Leu Pro Gly Val Thr Thr Ile Ser Met Thr Thr Asp Ser
        115                 120                 125

Ser Tyr Thr Thr Leu Gln Arg Val Ala Ala Leu Glu Arg Ser Gly Met
```

```
              130                 135                 140
Gln Ile Ser Arg His Ser Leu Tyr Leu Ala Leu Met Glu Phe Ser Gly
145                 150                 155                 160

Asn Thr Met Thr Arg Asp Ala Ser Arg Ala Val Leu Arg Phe Val Thr
                165                 170                 175

Val Thr Ala Glu Ala Leu Arg Phe Arg Gln Ile Gln Arg Glu Phe Arg
            180                 185                 190

Leu Ala Leu Ser Glu Thr Ala Pro Val Tyr Thr Met Thr Pro Asp Leu
        195                 200                 205

Thr Leu Asn Trp Gly Arg Ile Ser Asn Val Leu Pro Glu Tyr Arg Gly
    210                 215                 220

Glu Ala Gly Val Arg Val Gly Arg Ile Ser Phe Asn Asn Ile Ser Ala
225                 230                 235                 240

Ile Leu Gly Thr Val Ala Val Ile Leu Asn Cys His His Gln Gly Ala
                245                 250                 255

Arg Ser Val Arg Ala Glu Ser Gln Pro Glu Cys Gln Ile Thr Gly Asp
            260                 265                 270

Arg Pro Val Ile Lys Ile Asn Asn Thr Leu Trp Glu Ser Asn Thr Ala
        275                 280                 285

Ala Ala Phe Leu Asn Arg Lys Ser Gln Pro Leu Tyr Thr Thr Gly Glu
    290                 295                 300

<210> SEQ ID NO 3
<211> LENGTH: 84
<212> TYPE: PRT
<213> ORGANISM: Escherichia coli

<400> SEQUENCE: 3

Met Lys Lys Met Phe Ile Ala Val Leu Phe Ala Leu Val Ser Val Asn
1               5                   10                  15

Ala Met Ala Ala Asp Cys Ala Lys Gly Lys Ile Glu Phe Ser Lys Tyr
            20                  25                  30

Asn Glu Asp Asn Thr Phe Thr Val Lys Arg Glu Tyr Trp Thr Asn Arg
        35                  40                  45

Trp Asn Leu Gln Pro Leu Leu Gln Ser Ala Gln Leu Thr Gly Met Thr
    50                  55                  60

Val Thr Ile Ile Ser Asn Thr Cys Ser Ser Gly Ser Gly Phe Ala Gln
65                  70                  75                  80

Val Lys Phe Asn

<210> SEQ ID NO 4
<211> LENGTH: 959
<212> TYPE: DNA
<213> ORGANISM: Escherichia coli

<400> SEQUENCE: 4
atgaagtgta tattgttaaa gtggatactg tgtctgttac tgggttttc ttcggtatcc      60 tattcccagg agtttacgat agacttttcg actcaacaaa gttatgtatc ttcgttaaat    120
agtatacgga cagcgatatc gaccccctctt gaacatatat ctcagggagc tacatcggta   180
tccgttatta atcatacacc accaggaagt tatatttccg taggtatacg agggcttgat    240
gtttatcagg agcgttttga ccatcttcgt ctgattattg aacgaaataa tttatatgtg    300
gctggatttg ttaatacgac aacaaatact ttctacagat tttcagattt gcacatatat    360
cattgcccgg tgtgacaact atttccatga caacggacag cagttatacc actctgcaac    420
```

```
gtgtcgcagc gctggaacgt tccggaatgc aaatcagtcg tcactcactg gtttcatcat        480
atctggcgtt aatggagttc agtggtaata caatgaccag agatgcatca agagcagttc        540
tgcgttttgt cactgtcaca gcagaagcct tacggttcag gcaaatacag agagaatttc        600
gtctggcact gtctgaaact gctcctgttt atacgatgac gccggaagac gtggacctca        660
ctctgaactg ggggagaatc agcaatgtgc ttccggagta tcggggagag gctggtgtca        720
gagtggggag aatatccttt aataatatat cagcgatact tggtactgtg ccgttatac         780 tgaattgcca tcatcagggc gcacgttctg ttcgcgccgt gaatgaagag agtcaaccag        840
aatgtcagat aactggcgac aggcccgtta taaaaataaa caatacatta tgggaaagta        900
atacagcagc agcgtttctg aacagaaagt cacagccttt atatcaact ggtgaatga         959

<210> SEQ ID NO 5
<211> LENGTH: 213
<212> TYPE: DNA
<213> ORGANISM: Escherichia coli

<400> SEQUENCE: 5
atggcggcgg attgtgctaa aggtaaaatt gagttttcca gtataatga ggataatacc         60 tttactgtga aggtgtcagg aagagaatac tggacgaaca gatggaattt gcagccattg        120
ttacaaagtg ctcagctgac agggatgact gtaacaatca tatctaatac ctgcagttca        180
ggctcaggct ttgcccaggt gaagtttaac tga                                     213

<210> SEQ ID NO 6
<211> LENGTH: 213
<212> TYPE: DNA
<213> ORGANISM: Escherichia coli

<400> SEQUENCE: 6
atggcagcag attgcgctaa gggtaagatt gagttctcca gtacaacga ggataacacc         60 ttcacagtga aggtgtcagg aagggagtac tggacaaaca ggtggaactt gcaaccattg        120
ttgcaaagcg ctcaactcac agggatgaca gtgacaatca tctctaacac ctgcagctca        180
gggtcagggt tcgcccaagt gaagttcaac tga                                     213

<210> SEQ ID NO 7
<211> LENGTH: 213
<212> TYPE: DNA
<213> ORGANISM: Escherichia coli

<400> SEQUENCE: 7
atggcagcag attgtgcaaa aggtaaaatt gaattttcta aatataatga agataataca         60
tttacagtta aagtttctgg tagagaatat tggacaaata gatggaatct tcaaccactt        120
cttcaatctg cacaacttac aggtatgaca gttacaatta tttctaatac atgttcttct        180
ggttctggtt ttgcacaagt taaatttaat tga                                     213

<210> SEQ ID NO 8
<211> LENGTH: 213
<212> TYPE: DNA
<213> ORGANISM: Escherichia coli

<400> SEQUENCE: 8
atggccgccg actgcgccaa ggggaagatc gagttctcca gtacaacga ggacaacacc         60 ttcaccgtga aggtgtccgg gagggagtac tggaccaaca ggtggaacct ccagcccctc       120
ctccagtccg cccagctcac cgggatgacc gtgaccatca tctccaacac ctgctcctcc       180
```

```
gggtccgggt tcgcccaggt gaagttcaac tga                                 213

<210> SEQ ID NO 9
<211> LENGTH: 213
<212> TYPE: DNA
<213> ORGANISM: Escherichia coli

<400> SEQUENCE: 9
atggccgccg attgcgccaa gggtaagatc gaattctcca agtacaacga agataacact      60
ttcactgtta aggtttccgg tcgtgaatac tggactaacc gttggaacct ccaaccactc     120
ctccaatccg cccaactcac tggtatgact gttactatca tctccaacac ttgctcctcc     180
ggttccggtt tcgcccaagt taagttcaac tga                                 213

<210> SEQ ID NO 10
<211> LENGTH: 24
<212> TYPE: PRT
<213> ORGANISM: Nicotiana tabacum

<400> SEQUENCE: 10

Met Gly Arg Met Ser Ile Pro Met Met Gly Phe Val Val Leu Cys Leu
1               5                   10                  15

Trp Ala Val Val Ala Glu Gly Ser
            20

<210> SEQ ID NO 11
<211> LENGTH: 72
<212> TYPE: DNA
<213> ORGANISM: Nicotiana tabacum

<400> SEQUENCE: 11
atggggagaa tgtcaatacc catgatgggt tttgtggtgt tatgtctatg ggcagtggta      60
gcagaaggat cc                                                         72

<210> SEQ ID NO 12
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atttaactca gtattcagaa acaacaaaag ttcttctcta cataaaattt tcctatttta      60
gtgatcagtg aaggaaatca agaaaaataa atggggagaa tgtcaatacc catgatgggt     120
tttgtggtgt tatgtctatg ggcagtggta gcagaaggat ccgcggcgga ttgtgctaaa     180
ggtaaaattg agttttccaa gtataatgag gataatacct ttactgtgaa ggtgtcagga     240
agagaatact ggacgaacag atggaatttg cagccattgt tacaaagtgc tcagctgaca     300
gggatgactg taacaatcat atctaatacc tgcagttcag gctcaggctt tgcccaggtg     360
aagtttaact ga                                                        372

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      signal peptide
```

```
<400> SEQUENCE: 13

Lys Asp Glu Leu
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      signal peptide

<400> SEQUENCE: 14

His Asp Glu Leu
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      signal peptide

<400> SEQUENCE: 15

Lys Asp Glu Phe
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      signal peptide

<400> SEQUENCE: 16

His Asp Glu Phe
1

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      signal peptide

<400> SEQUENCE: 17

Arg Ser Glu His Asp Glu Leu
1               5

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA sequence coding a signal peptide

<400> SEQUENCE: 18
agatctgaac atgatgaatt g                                              21

<210> SEQ ID NO 19
<211> LENGTH: 7
<212> TYPE: PRT
<213> ORGANISM: Nicotiana tabacum
```

<400> SEQUENCE: 19

Asp Leu Leu Val Asp Thr Met
1               5

<210> SEQ ID NO 20
<211> LENGTH: 21
<212> TYPE: DNA
<213> ORGANISM: Nicotiana tabacum

<400> SEQUENCE: 20
gatttgttgg ttgatactat g                                             21

<210> SEQ ID NO 21
<211> LENGTH: 15
<212> TYPE: PRT
<213> ORGANISM: Armoracia rusticana

<400> SEQUENCE: 21

Leu Leu His Asp Met Val Glu Val Val Asp Phe Val Ser Ser Met
1               5                   10                  15

<210> SEQ ID NO 22
<211> LENGTH: 45
<212> TYPE: DNA
<213> ORGANISM: Armoracia rusticana

<400> SEQUENCE: 22
ctactccatg atatggtgga ggtcgttgac tttgttagct ctatg                   45

<210> SEQ ID NO 23
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
atttaactca gtattcagaa acaacaaaag ttcttctcta cataaaattt tcctatttta    60
gtgatcagtg aaggaaatca agaaaaataa atggggagaa tgtcaatacc catgatgggt  120
tttgtggtgt tatgtctatg ggcagtggta gcagaaggat ccgcggcgga ttgtgctaaa  180
ggtaaaattg agttttccaa gtataatgag gataataccc ttactgtgaa ggtgtcagga  240
agagaatact ggacgaacag atggaatttg cagccattgt tacaaagtgc tcagctgaca  300
gggatgactg taacaatcat atctaatacc tgcagttcag gctcaggctt tgcccaggtg  360
aagtttaaca gatctgaaca tgatgaattg tga                              393

<210> SEQ ID NO 24
<211> LENGTH: 432
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
atttaactca gtattcagaa acaacaaaag ttcttctcta cataaaattt tcctatttta    60
gtgatcagtg aaggaaatca agaaaaataa atggggagaa tgtcaatacc catgatgggt  120
tttgtggtgt tatgtctatg ggcagtggta gcagaaggat cttatcctta tgattatcct  180

```
gattatgctg gatccgcggc ggattgtgct aaaggtaaaa ttgagttttc caagtataat      240
gaggataata cctttactgt gaaggtgtca ggaagagaat actggacgaa cagatggaat      300
ttgcagccat tgttacaaag tgctcagctg acagggatga ctgtaacaat catatctaat      360
acctgcagtt caggctcagg ctttgcccag gtgaagttta acagatctga tttgttggtt      420
gatactatgt ga                                                         432

<210> SEQ ID NO 25
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aatctagagt ctatttaact cagtattcag aaacaacaaa a                          41

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aaatgcatta tttttcttga tttccttcac                                       30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aaatgcatgg ggagaatgtc aatacccatg                                       30

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ttgaattctc cttctgctac cactgccca                                        29

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gatgcatgaa ttcagtaaag gagaagaact                                       30

<210> SEQ ID NO 30
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 30
gttatttgta tagttcatcc atgccatgtg                                    30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gttaaagctc atcatgctct ttgtatagtt                                    30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aaatgcatgg cctccatctc ctcctcagcc                                    30

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ttgaattcta ggtatgaaag agtctcgta                                     29

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtcgacggta cccccgggga gct                                           23

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35 ccccggggt accgtcgaca gct                                            23

<210> SEQ ID NO 36
<211> LENGTH: 38
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 36
tatctagagc caccatggga tccgcggcgg attgtgct                              38

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ttcaagatct gttaaacttc acctgggcaa                                       30

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tataggatcc cattattttt cttgatttcc                                       30

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tatatctaga gccaccatgg ggagaatgtc                                       30

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tataggatcc cattattttt cttgatttcc                                       30

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gatctgaaca tgatgaattg t                                                21

<210> SEQ ID NO 42
<211> LENGTH: 21
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 42
gatcacaatt catcatgttc a                                              21

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gatctgattt gttggttgat actatgt                                        27

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gatcacatag tatcaaccaa caaatca                                        27

<210> SEQ ID NO 45
<211> LENGTH: 75
<212> TYPE: PRT
<213> ORGANISM: Lactuca sativa

<400> SEQUENCE: 45

Met Ala Ser Ile Ser Ser Ser Ala Ile Ala Thr Val Asn Arg Thr Thr
1               5                   10                  15

Ser Thr Gln Ala Ser Leu Ala Ala Pro Phe Thr Gly Leu Lys Ser Asn
            20                  25                  30

Val Ala Phe Pro Val Thr Lys Lys Ala Asn Asn Asp Phe Ser Ser Leu
        35                  40                  45

Pro Ser Asn Gly Gly Arg Val Gln Cys Met Lys Val Trp Pro Pro Ile
    50                  55                  60

Gly Leu Lys Lys Tyr Glu Thr Leu Ser Tyr Leu
65                  70                  75

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tttggatcct aggtatgaaa gagtctcgta                                     30

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gatcttatcc ttatgattat cctgattatg ctg                                    33

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gatccagcat aatcaggata atcataagga taa                                    33

<210> SEQ ID NO 49
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
atggcagcag attgcgctaa gggtaagatt gagttctcca agtacaacga ggat             54

<210> SEQ ID NO 50
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ctcccttcct gacaccttca ctgtgaaggt gttatcctcg ttgta                       45

<210> SEQ ID NO 51
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tcaggaaggg agtactggac aaacaggtgg aacttgcaac cattg                       45

<210> SEQ ID NO 52
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cactgtcatc cctgtgagtt gagcgctttg caacaatggt tgcaa                       45

<210> SEQ ID NO 53
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53

```
gggatgacag tgacaatcat ctctaacacc tgcagctcag ggtca                45
```

<210> SEQ ID NO 54
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54

```
tcagttgaac ttcacttggg cgaaccctga ccctgagct                       39
```

<210> SEQ ID NO 55
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55

```
atggcagcag attgtgcaaa aggtaaaatt gaattttcta aatataatga agat      54
```

<210> SEQ ID NO 56
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56

```
ttctctacca gaaactttaa ctgtaaatgt attatcttca ttata                45
```

<210> SEQ ID NO 57
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57

```
tctggtagag aatattggac aaatagatgg aatcttcaac cactt                45
```

<210> SEQ ID NO 58
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58

```
aactgtcata cctgtaagtt gtgcagattg aagaagtggt tgaag                45
```

<210> SEQ ID NO 59
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59

```
ggtatgacag ttacaattat ttctaataca tgttcttctg gttct                45
```

<210> SEQ ID NO 60
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tcaattaaat ttaacttgtg caaaaccaga accagaaga                    39

<210> SEQ ID NO 61
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
atggccgccg actgcgccaa ggggaagatc gagttctcca agtacaacga ggac    54

<210> SEQ ID NO 62
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ctccctcccg gacaccttca cggtgaaggt gttgtcctcg ttgta             45

<210> SEQ ID NO 63
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tccgggaggg agtactggac caacaggtgg aacctccagc ccctc             45

<210> SEQ ID NO 64
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cacggtcatc ccggtgagct gggcggactg gaggaggggc tggag             45

<210> SEQ ID NO 65
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gggatgaccg tgaccatcat ctccaacacc tgctcctccg ggtcc             45

<210> SEQ ID NO 66
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
tcagttgaac ttcacctggg cgaacccgga cccggagga                                39

<210> SEQ ID NO 67
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
atggccgccg attgcgccaa gggtaagatc gaattctcca agtacaacga agat              54

<210> SEQ ID NO 68
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ttcacgaccg gaaaccttaa cagtgaaagt gttatcttcg ttgta                        45

<210> SEQ ID NO 69
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
tccggtcgtg aatactggac taaccgttgg aacctccaac cactc                        45

<210> SEQ ID NO 70
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
aacagtcata ccagtgagtt gggcggattg gaggagtggt tggag                        45

<210> SEQ ID NO 71
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ggtatgactg ttactatcat ctccaacact tgctcctccg gttcc                        45

```
<210> SEQ ID NO 72
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tcagttgaac ttaacttggg cgaaaccgga accggagga                          39

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tttggatccc aggagtttac gatagacttt                                   30

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tttagatctt tcaccagttg tatataaagg                                   30

<210> SEQ ID NO 75
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
atttaactca gtattcagaa acaacaaaag ttcttctcta cataaaattt tcctatttta    60
gtgatcagtg aaggaaatca agaaaaataa atggggagaa tgtcaatacc catgatgggt   120
tttgtggtgt tatgtctatg ggcagtggta gcagaaggat ccgcagcaga ttgcgctaag   180
ggtaagattg agttctccaa gtacaacgag gataacacct tcacagtgaa ggtgtcagga   240
agggagtact ggacaaacag gtggaacttg caaccattgt tgcaaagcgc tcaactcaca   300
gggatgacag tgacaatcat ctctaacacc tgcagctcag ggtcagggtt cgcccaagtg   360
aagttcaaca gatctgaaca tgatgaattg tga                               393

<210> SEQ ID NO 76
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
atttaactca gtattcagaa acaacaaaag ttcttctcta cataaaattt tcctatttta    60
gtgatcagtg aaggaaatca agaaaaataa atggggagaa tgtcaatacc catgatgggt   120
tttgtggtgt tatgtctatg ggcagtggta gcagaaggat ccgcagcaga ttgtgcaaaa   180
```

```
ggtaaaattg aatttctaa atataatgaa gataatacat ttacagttaa agtttctggt      240
agagaatatt ggacaaatag atggaatctt caaccacttc ttcaatctgc acaacttaca     300
ggtatgacag ttacaattat ttctaataca tgttcttctg gttctggttt tgcacaagtt    360
aaatttaata gatctgaaca tgatgaattg tga                                  393
```

<210> SEQ ID NO 77
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
atttaactca gtattcagaa acaacaaaag ttcttctcta cataaaattt tcctatttta     60
gtgatcagtg aaggaaatca agaaaataa atggggagaa tgtcaatacc catgatgggt     120
tttgtggtgt tatgtctatg gcagtggta gcagaaggat ccgccgccga ctgcgccaag     180
gggaagatcg agttctccaa gtacaacgag acaacacct tcaccgtgaa ggtgtccggg     240
agggagtact ggaccaacag gtggaacctc cagcccctcc tccagtccgc ccagctcacc     300
gggatgaccg tgaccatcat ctccaacacc tgctcctccg ggtccgggtt cgcccaggtg     360
aagttcaaca gatctgaaca tgatgaattg tga                                  393
```

<210> SEQ ID NO 78
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78

```
atttaactca gtattcagaa acaacaaaag ttcttctcta cataaaattt tcctatttta     60
gtgatcagtg aaggaaatca agaaaataa atggggagaa tgtcaatacc catgatgggt    120
tttgtggtgt tatgtctatg gcagtggta gcagaaggat ccgccgccga ttgcgccaag    180
ggtaagatcg aattctccaa gtacaacgaa gataacactt tcactgttaa ggtttccggt    240
cgtgaatact ggactaaccg ttggaacctc caaccactcc tccaatccgc ccaactcact    300
ggtatgactg ttactatcat ctccaacact tgctcctccg gttccggttt cgcccaagtt    360
aagttcaaca gatctgaaca tgatgaattg tga                                  393
```

<210> SEQ ID NO 79
<211> LENGTH: 213
<212> TYPE: DNA
<213> ORGANISM: Escherichia coli

<400> SEQUENCE: 79

```
atggcggcgg actgcgcgaa gggcaagatc gagttctcga agtacaacga ggacaacacg      60
ttcacggtca aggtctcggg ccgcgagtac tggacgaacc gctggaacct gcagccgctg     120
ctgcagtcgg cgcagctgac gggcatgacg gtcacgatca tctcgaacac gtgctcgtcg     180
ggctcgggct cgcgcaggt caagttcaac tga                                   213
```

<210> SEQ ID NO 80
<211> LENGTH: 54
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 80
atggcggcgg actgcgcgaa gggcaagatc gagttctcga agtacaacga ggac          54

<210> SEQ ID NO 81
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ctcgcggccc gagaccttga ccgtgaacgt gttgtcctcg ttgta                    45

<210> SEQ ID NO 82
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tcgggccgcg agtactggac gaaccgctgg aacctgcagc cgctg                    45

<210> SEQ ID NO 83
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gaccgtcatg cccgtcagct gcgccgactg cagcagcggc tgcag                    45

<210> SEQ ID NO 84
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ggcatgacgg tcacgatcat ctcgaacacg tgctcgtcgg gctcg                    45

<210> SEQ ID NO 85
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tcagttgaac ttgacctgcg cgaagcccga gcccgacga                           39

<210> SEQ ID NO 86
<211> LENGTH: 396
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 86
atttaactca gtattcagaa acaacaaaag ttcttctcta cataaaattt tcctatttta         60
gtgatcagtg aaggaaatca agaaaaataa atggggagaa tgtcaatacc catgatgggt        120
tttgtggtgt tatgtctatg ggcagtggta gcagaaggat ccatggcggc ggactgcgcg        180
aagggcaaga tcgagttctc gaagtacaac gaggacaaca cgttcacggt caaggtctcg        240
ggccgcgagt actggacgaa ccgctggaac ctgcagccgc tgctgcagtc ggcgcagctg        300
acgggcatga cggtcacgat catctcgaac acgtgctcgt cgggctcggg cttcgcgcag        360
gtcaagttca acagatctga acatgatgaa ttgtga                                 396
```